(12) United States Patent
Bittman et al.

(10) Patent No.: US 8,153,615 B2
(45) Date of Patent: Apr. 10, 2012

(54) SYNTHESIS OF GLYCEROLIPID CARBAMATES AND DICARBAMATES AND THEIR USE AS AN ANTITUMOR COMPOUNDS

(76) Inventors: Robert Bittman, Roslyn Heights, NY (US); Hoe-Sup Byun, Bayside, NY (US); Gilbert Arthur, Winnipeg (CA)

( * ) Notice: Subject to any disclaimer, the term of this patent is extended or adjusted under 35 U.S.C. 154(b) by 799 days.

(21) Appl. No.: 11/917,025

(22) PCT Filed: Jun. 12, 2006

(86) PCT No.: PCT/CA2006/000962
§ 371 (c)(1),
(2), (4) Date: Jun. 20, 2008

(87) PCT Pub. No.: WO2006/130994
PCT Pub. Date: Dec. 14, 2006

(65) Prior Publication Data
US 2009/0042811 A1  Feb. 12, 2009

Related U.S. Application Data

(60) Provisional application No. 60/689,065, filed on Jun. 10, 2005.

(51) Int. Cl.
*A01N 57/26* (2006.01)
*A61K 31/685* (2006.01)
*A01N 43/04* (2006.01)
*A61K 31/70* (2006.01)

(52) U.S. Cl. ...................................................... 514/78

(58) Field of Classification Search .................. None
See application file for complete search history.

(56) References Cited

FOREIGN PATENT DOCUMENTS

| CA | 1152068 | 8/1983 |
|---|---|---|
| CA | 1261342 | 9/1989 |

OTHER PUBLICATIONS

Surles et al. J. Org. Chem. 1988, 53, 899-901.*
Bittman et al. J. Med. Chem. 1994, 37, 425-430.*
Lohmeyer et al "Phospholipid Antitumor Agents" Medicinal Research Reviews, 1995 15(3), 157-223.
Houlihan et al "Phospholipid antitumor agents" Medicinal Research Reviews, 1995 15(3), 157-223.
Berdel et al Synthetic Alkyl-phospholipid analogs: a new class of antitumor agents in: Phospholipids and cellular Regulations Vo. II Edited by J.F. Kuo; Boca Raton CRC Press 1985 pp. 41-73.
Mollinedo et al ET-180CH3 (Edelfosine) a selective antitumor lipid targeting apoptosis through intracellular activation of Fas/CD95 death receptor: Current Medicinal Chemistry 2004, 11, 3163-3184.

* cited by examiner

*Primary Examiner* — Layla Bland
(74) *Attorney, Agent, or Firm* — Ade & Company Inc; Michael R Williams

(57) ABSTRACT

The syntheses and in vitro antitumor properties of carbamate-containing, dicarbamate-containing, and ureido-containing phospholipid compounds that have an ether linkage at the C-1 position of a glycerol backbone, a carbamate, dicarbamate, or ureido moiety at the C-2 position of the glycerol backbone, and a phosphocholine, phosphonocholine, or glycoside moiety at the C-3 position of the glycerol backbone are described. The synthesis and antiproliferative activity of ether lipids with a naphthol moiety at the C-1 position are also described. These compounds were shown to be potent inhibitors of cancer cell growth. These compounds are useful for killing cancer cells and treating cancer.

6 Claims, 9 Drawing Sheets

Fig. 1. The structures of the carbamate-containing and dicarbamate-containing ether-linked glycerophospholipids disclosed in this invention are:

Figure 7. Reaction Scheme for the Synthesis of Carbamate Phosphonocholine (Compound II) and Dicarbamate Phosphonocholine (Compound V) from 1,3-O-Benzylidine-1,3,4-butanetriol (2)
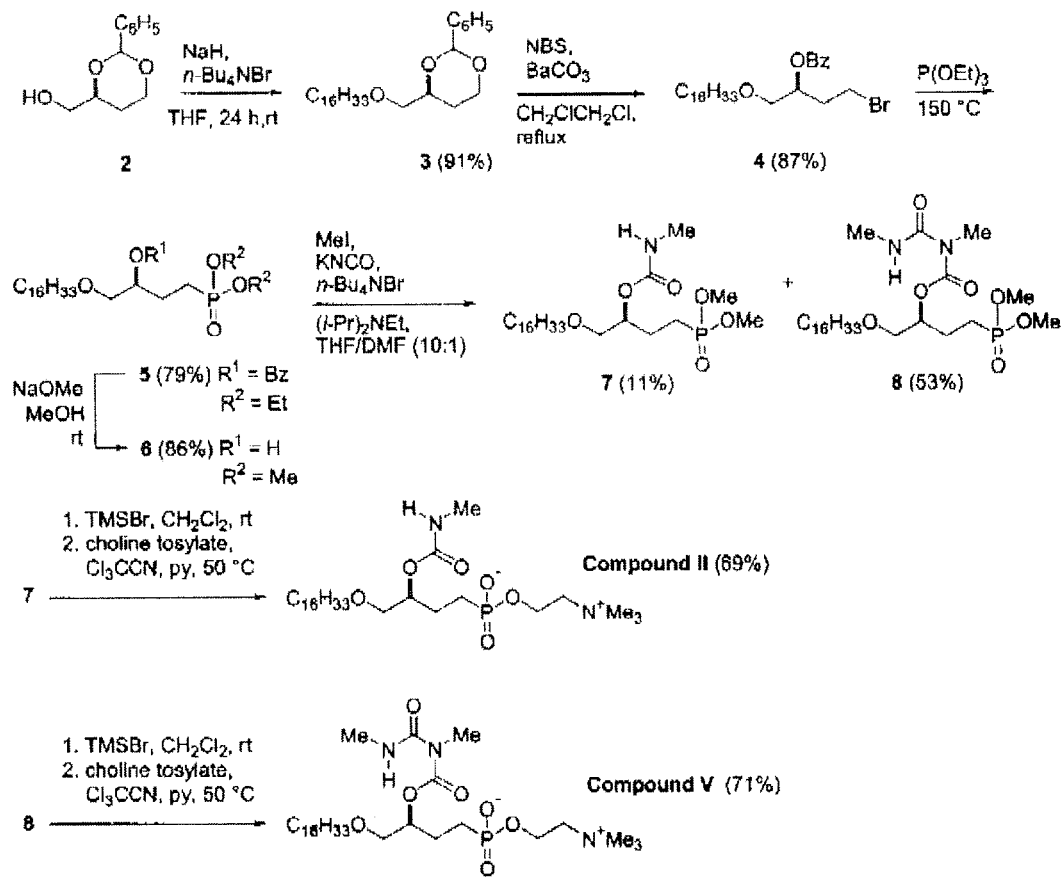
Figure 8. Reaction Scheme for the Synthesis of Carbamido Phosphorylcholine (Compound III) from 3-O-Hexadecyl-sn-glycerol (2)
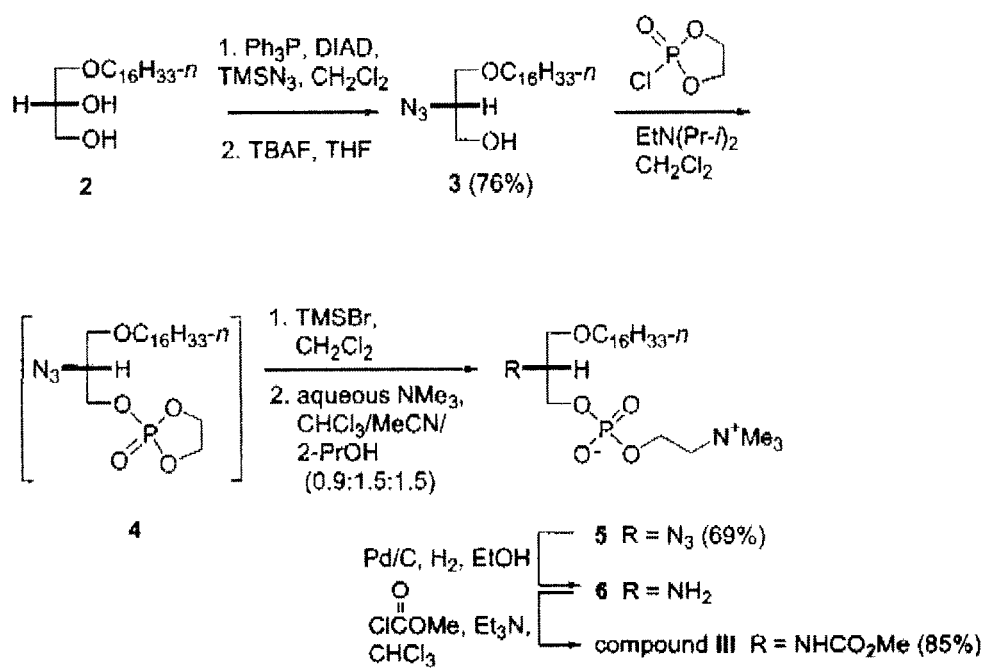

1-O-(7-N, N-dimethylamino-3-pentadecanoyl-1-naphthyl)-2-O-methyl-sn-glycero-3-phosphocholine Cytotoxic Effect of Compound I on DU145 and PC3 cells

SYNTHESIS OF GLYCEROLIPID CARBAMATES AND DICARBAMATES AND THEIR USE AS AN ANTITUMOR COMPOUNDS

PRIOR APPLICATION INFORMATION

This application claims the benefit of U.S. Provisional Application 60/689,065, filed Jun. 10, 2005.

BACKGROUND OF THE INVENTION

Prostate cancer (PCa) is the most common male cancer and the second leading cause of cancer deaths in males (Jemal et al., 2003, Cancer Statistics. CA Cancer J. Clin. 53, 5-26). Although androgen deprivation is initially effective, it does not cure the disease, and invariably the tumor recurs in an androgen-independent form that is resistant to classical chemotherapy, and usually metastasizes primarily to the bone (Saitoh et al., 1984, Cancer 54, 3078-3084; Jacobs, 1983, Urology 21, 337-344). The molecular events underlying the progression of the disease have yet to be elucidated; however, it is clear that once the disease progresses it does not respond to the current array of chemotherapeutic agents (Koutsilieras and Tolis, 1985, Prostate 7, 31-39). There is, therefore, a clear need to develop new agents that kill hormone-independent prostate tumor cells and/or prevent their metastases.

A group of antitumor compounds collectively known as antitumor ether lipids (AELs) act by perturbing intracellular signaling pathways, leading to the killing of the cells (Arthur and Bittman, 1998, Biochim. Biophys. Acta 1390, 85-102; Bittman and Arthur, 1999, In Liposomes: Rational Design, A. S. Janoff, Ed., Marcel Dekker, New York, pp. 125-144). These compounds are long-lived analogs of the naturally occurring phospholipid, lysophosphatidylcholine (LPC). Insertion of two ether bonds into LPC in place of the usual two ester bonds gives an analog that is highly resistant to metabolism at sites other than in the vicinity of the phosphodiester linkage. AELs have the potential to deliver antitumor activity without any mutagenicity because, unlike many other anticancer agents, they do not interact directly with DNA. They possess cell-selective effects by inhibiting the proliferation and killing of cancer cells at concentrations that do not affect normal cells (Berdel, 1991, Br. J. Cancer 64, 208-211; Samadder and Arthur, 1999, Cancer Res. 59, 4808-4815). The prototype or gold standard AEL is known as 1-O-octadecyl-2-O-methyl-glycerophosphocholine (ET-18-OCH$_3$), which inhibits a broad panel of tumor cell lines (Berdel et al., 1985, in Phospholipids and Cellular Regulation, Kuo, J. F., ed., Vol. 2, pp 41-73, CRC Press, Boca Raton, Fla.; Lohmeyer and Bittman, 1994, Drugs Future 19, 1021-1037; Houlihan et al., 1995, Med. Res. Rev. 15, 157-223; Mollinedo et al., 2004, Curr. Med. Chem. 2004, 11, 3163-3184) but it exhibits no known selectivity against specific cancer cell types.

SUMMARY OF THE INVENTION

According to a first aspect of the invention, there is provided a compound having a formula selected from the group consisting of:

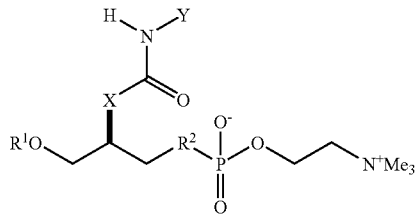

X = O or NH
Y = Me or OH
R$^1$ = C$_{12}$-C$_{20}$ alkyl or C$_{12}$-C$_{20}$ alkenyl
R$^2$ = O or CH$_2$ -continued

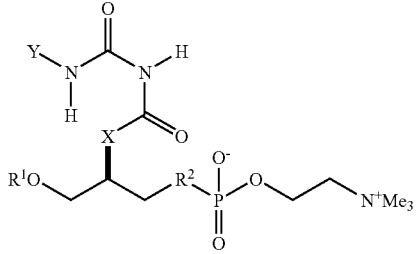

X = O or NH
Y = Me or OH
R$^1$ = C$_{12}$-C$_{20}$ alkyl or C$_{12}$-C$_{20}$ alkenyl
R$^2$ = O or CH$_2$

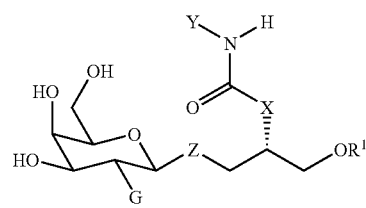

X, Y, and R$^1$ as above
Z = O or CH$_2$
G = OH, H, or NH$_2$

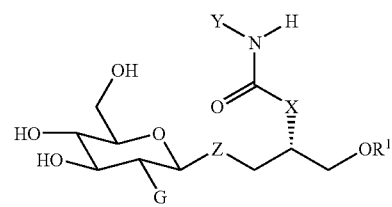

X, Y, and R$^1$ as above
Z = O or CH$_2$
G = OH, H, or NH$_2$

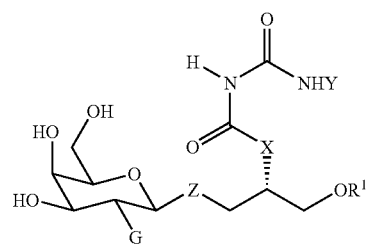

X, Y, and R$^1$ as above
Z = O or CH$_2$
G = OH, H, or NH$_2$

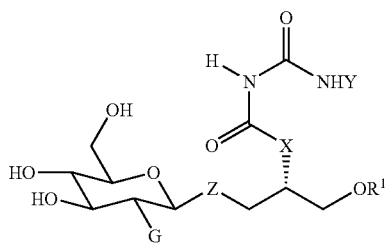

X, Y, and R¹ as above
Z = O or CH₂
G = OH, H, or NH₂

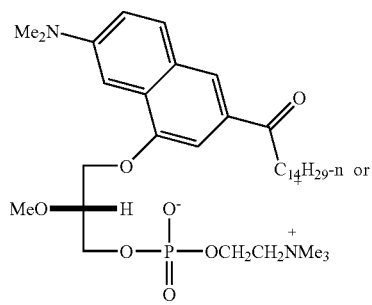

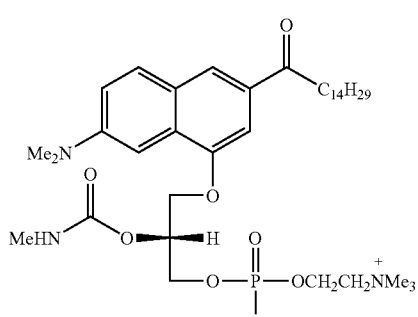

According to a second aspect of the invention, there is provided the use of a compound having a formula selected from the group consisting of:

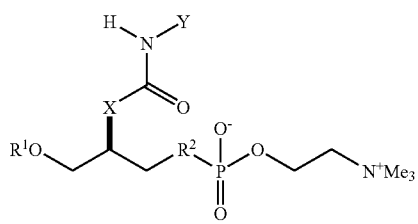

X = O or NH
Y = Me or OH
R¹ = $C_{12}$-$C_{20}$ alkyl or $C_{12}$-$C_{20}$ alkenyl
R² = O or CH₂

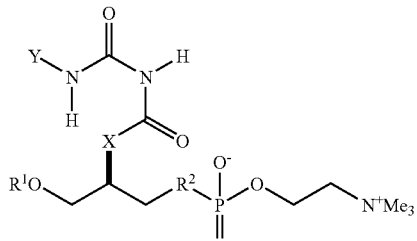

X = O or NH
Y = Me or OH
R¹ = $C_{12}$-$C_{20}$ alkyl or $C_{12}$-$C_{20}$ alkenyl
R² = O or CH₂

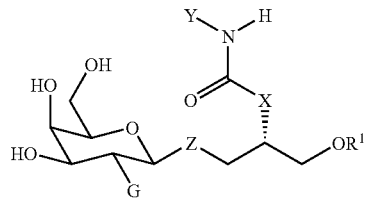

X, Y, and R¹ as above
Z = O or CH₂
G = OH, H, or NH₂

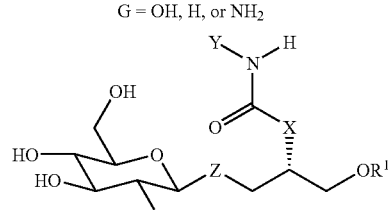

X, Y, and R¹ as above
Z = O or CH₂
G = OH, H, or NH₂

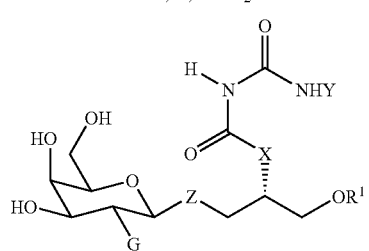

X, Y, and R¹ as above
Z = O or CH₂
G = OH, H, or NH₂

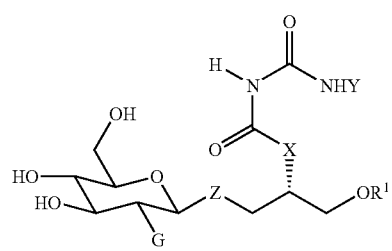

X, Y, and R¹ as above
Z = O or CH₂
G = OH, H, or NH₂

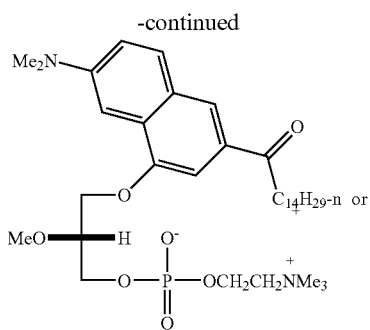

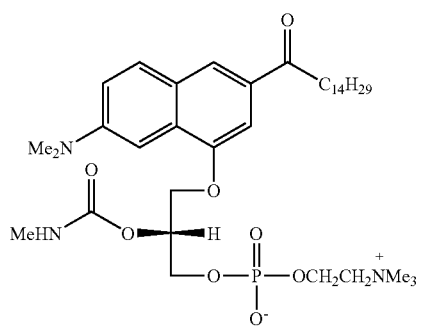

in preparation of a medicament for treating cancer.

According to a third aspect of the invention, there is provided a method of treating cancer in a patient comprising administering to a patient in need of such treatment an effect amount of a compound having a formula selected from the group consisting of:

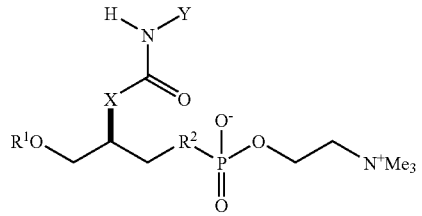

X = O or NH
Y = Me or OH
$R^1$ = $C_{12}$-$C_{20}$ alkyl or $C_{12}$-$C_{20}$ alkenyl
$R^2$ = O or $CH_2$

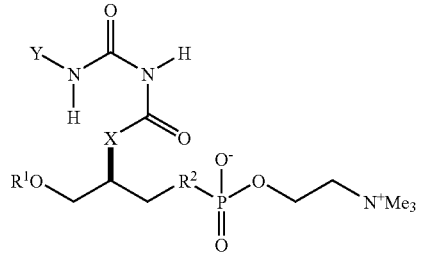

X = O or NH
Y = Me or OH
$R^1$ = $C_{12}$-$C_{20}$ alkyl or $C_{12}$-$C_{20}$ alkenyl
$R^2$ = O or $CH_2$

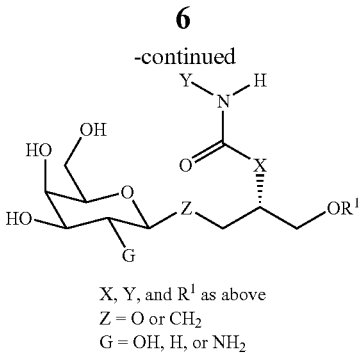

X, Y, and $R^1$ as above
Z = O or $CH_2$
G = OH, H, or $NH_2$

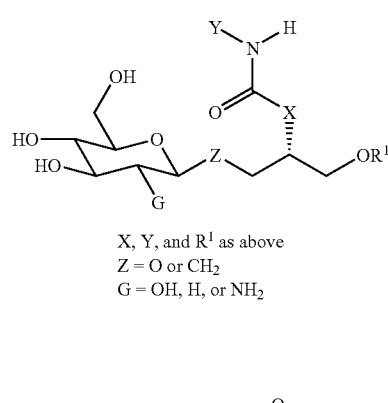

X, Y, and $R^1$ as above
Z = O or $CH_2$
G = OH, H, or $NH_2$

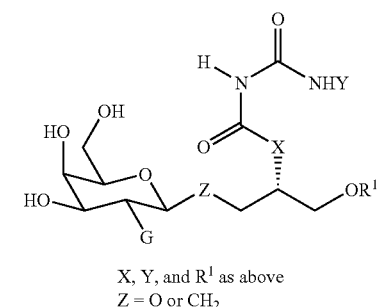

X, Y, and $R^1$ as above
Z = O or $CH_2$
G = OH, H, or $NH_2$

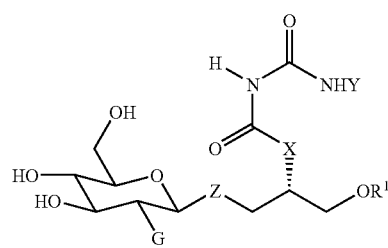

X, Y, and $R^1$ as above
Z = O or $CH_2$
G = OH, H, or $NH_2$

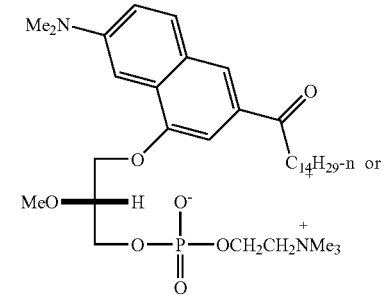

-continued

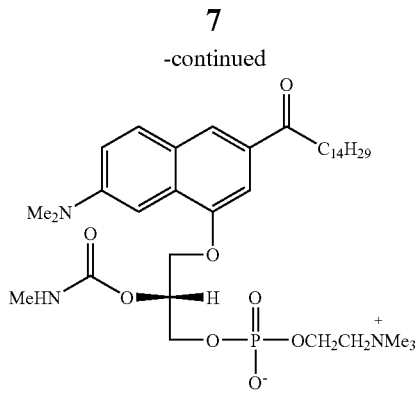

BRIEF DESCRIPTION OF THE DRAWINGS

FIG. 7 is a reaction scheme for the synthesis of carbamate phosphonocholine (compound II) and dicarbamate phosphonocholine (compound V) from 1,3-O-benzylidine-1,3,4-butanetriol.

FIG. 8 is a reaction scheme for the synthesis of carbamate phosphorylcholine (compound III) from 3-O-hexadecyl-sn-glycerol.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Figure 1:
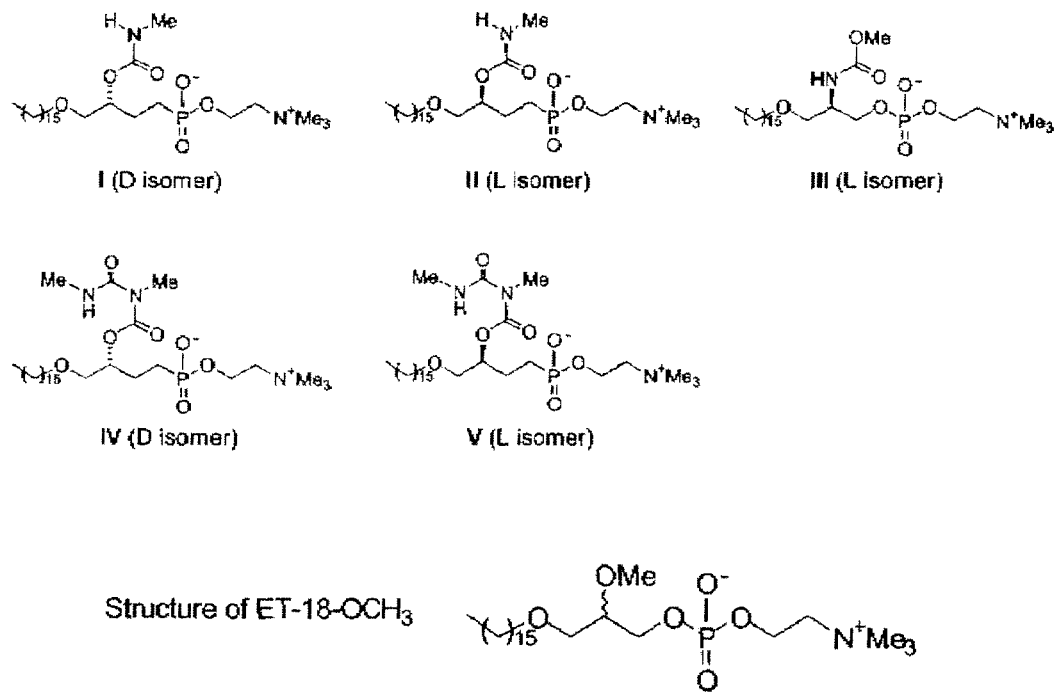
FIG. 1 shows the structures of the carbamate lipids (compounds I, II, and III) and dicarbamate lipids (compounds IV and V) of the invention. The structure of the "gold standard" antitumor ether lipid ET-18-OCH$_3$ is shown for comparison.

We synthesized analogs of ET-18-OCH$_3$ with a carbamate (compounds I, II, and III) or a dicarbamate (compounds IV and V) moiety at the C-2 position instead of the OMe group in ET-18-OCH$_3$ (shown in FIG. 1). Four of the analogs (compounds I, II, IV, and V) have a phosphonocholine head group at the C-3 position instead of the phosphocholine as in ET-18-OCH$_3$ and compound III (FIG. 1). The phosphonate moiety was employed in order to resist the action of phospholipases, which are ubiquitous in cells and could cause the breakdown of the compounds more rapidly than is desired. We also synthesized both the D (compounds I and IV) and L (compounds II, III, and V) stereoisomers of these compounds.

Other substituents that can be made are a ureido analog with urea or a hydroxyureido analog with hydroxyurea at the C2 position. Additional analogs are carbamates in which the sn-3 phosphonocholine group is replaced with a C-glycoside to yield glycosylated carbamates, and a carbamate with a naphthol moiety at the C-1 position. A scheme that outlines the synthesis of these C-glycosides and the naphthol analog appears herein. The figure below depicts general structures for the compounds of the invention:

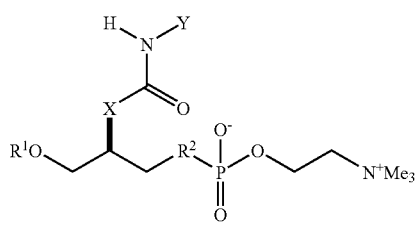

X = O or NH
Y = Me or OH
R¹ = $C_{12}$-$C_{20}$ alkyl or $C_{12}$-$C_{20}$ alkenyl
R² = O or $CH_2$

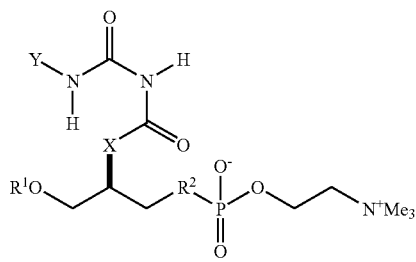

X = O or NH
Y = Me or OH
R¹ = $C_{12}$-$C_{20}$ alkyl or $C_{12}$-$C_{20}$ alkenyl
R² = O or $CH_2$

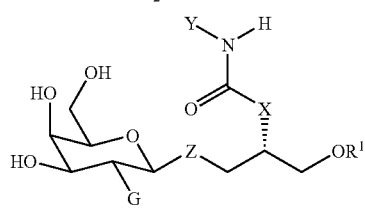

X, Y, and R¹ as above
Z = O or $CH_2$
G = OH, H, or $NH_2$

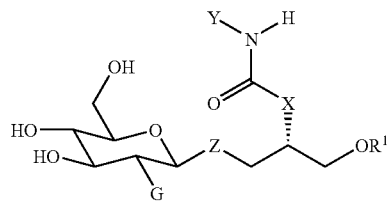

X, Y, and R¹ as above
Z = O or $CH_2$
G = OH, H, or $NH_2$

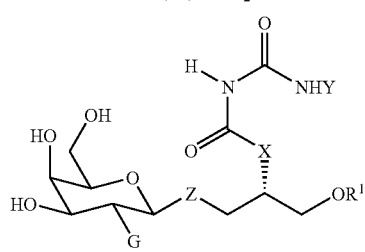

X, Y, and R¹ as above
Z = O or $CH_2$
G = OH, H, or $NH_2$

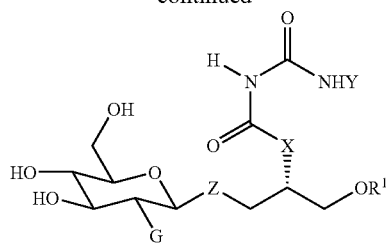

X, Y, and R¹ as above
Z = O or $CH_2$
G = OH, H, or $NH_2$

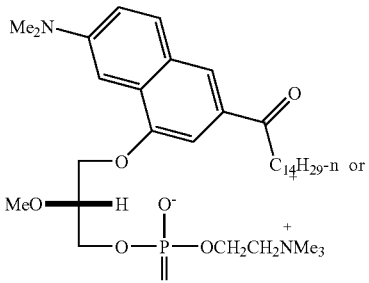

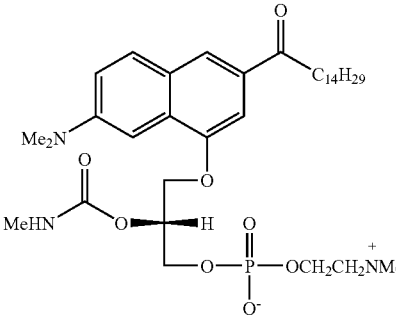

Figure 2:
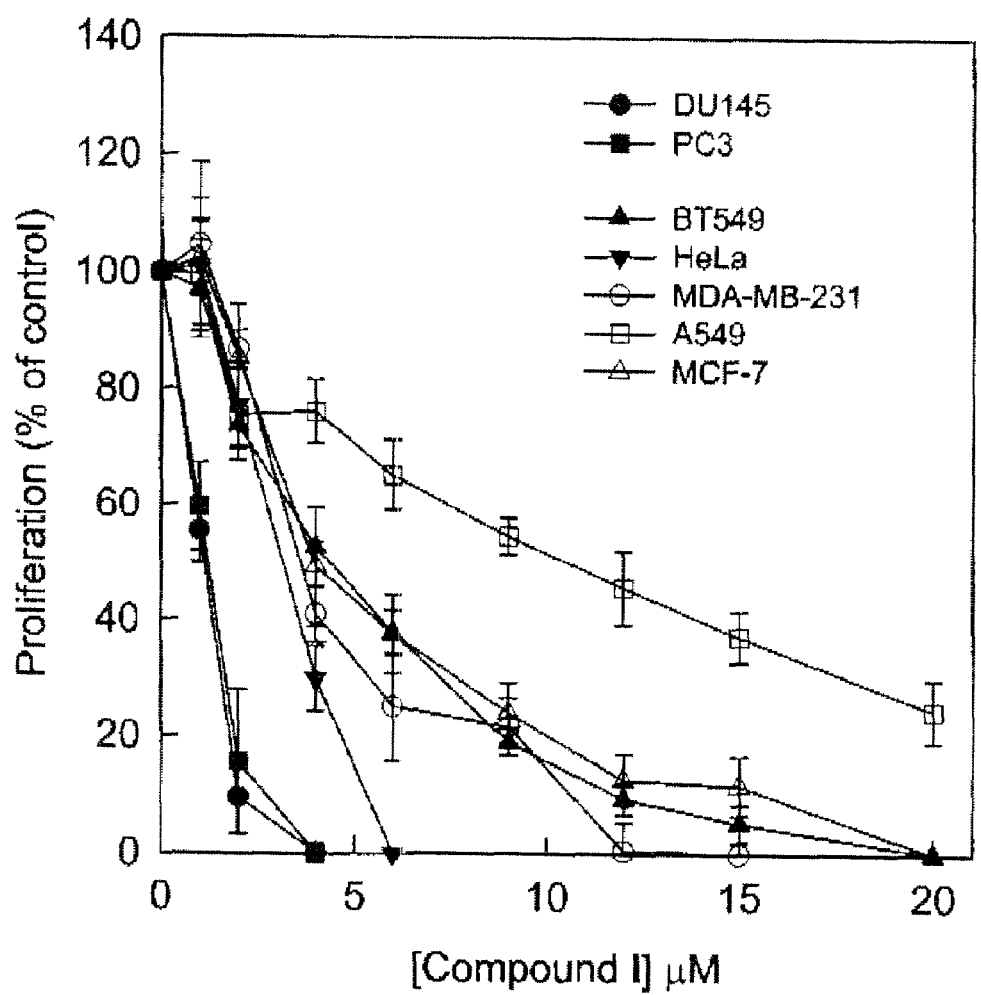
FIG. 2 is a graphical depiction of the results of an antiproliferative evaluation of compound I against the following cancer cell lines: DU145, PC3, BT549, HeLa, MDA-MB-231, A549, and MCF-7. Cells growing exponentially in 48-well plates were incubated with different concentrations of compound I for 48 h. The increases in cell numbers were determined by the CyQuant assay and are expressed as a percentage of the increase in control wells with the vehicle (0.1% ethanol). The results are the average+SD from six different wells.
Figure 3:
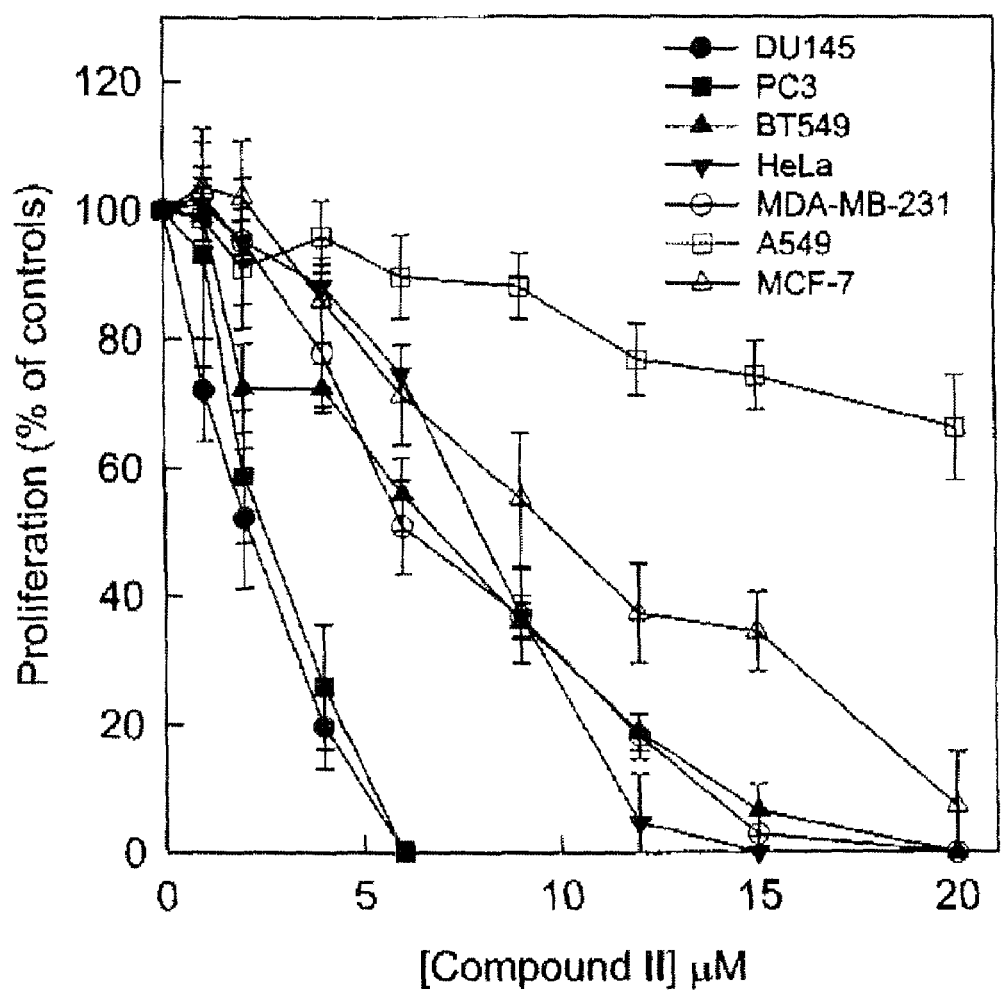
FIG. 3 is a graphical depiction of the results of an antiproliferative evaluation of compound II against the following cancer cell lines: DU145, PC3, BT549, HeLa, MDA-MB-231, A549, and MCF-7. Cells growing exponentially in 48-well plates were incubated with different concentrations of compound II for 48 h. The increases in cell numbers were determined by the CyQuant assay and are expressed as a percentage of the increase in control wells with the vehicle (0.1% ethanol). The results are the average+SD from six different wells.
Figure 4:
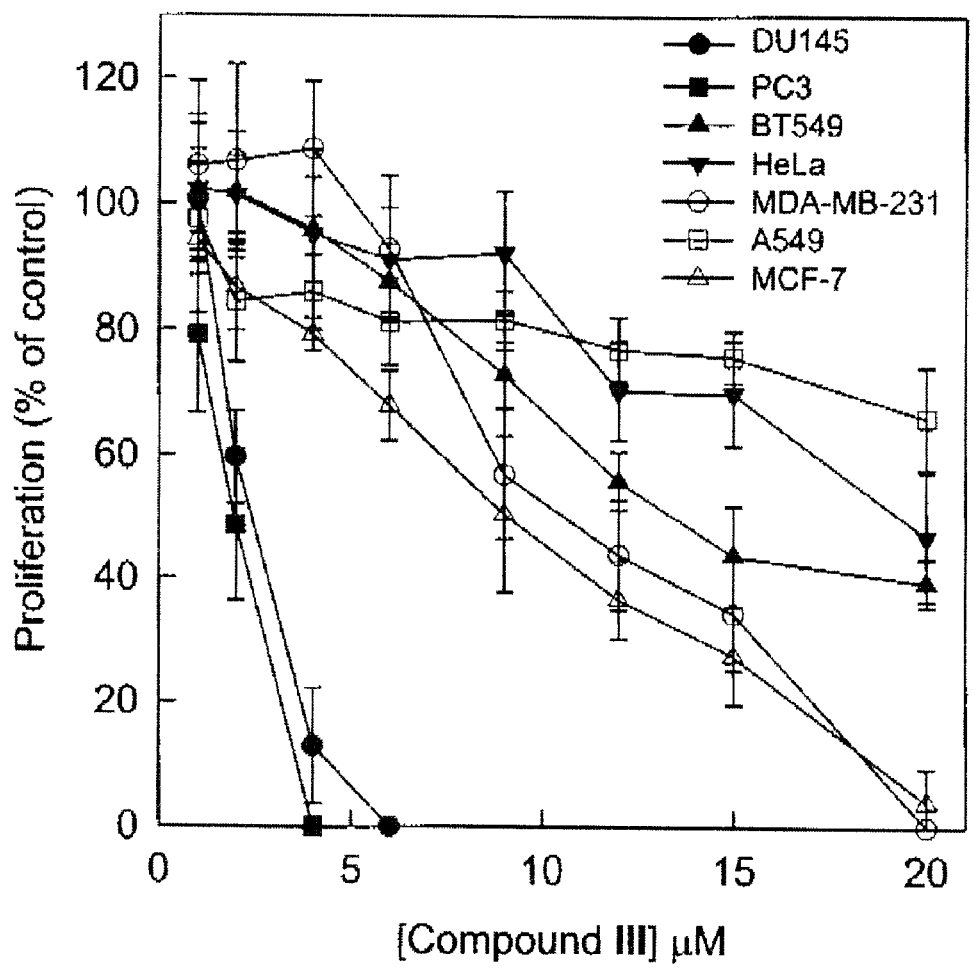
FIG. 4 is a graphical depiction of the results of an antiproliferative evaluation of compound III against the following cancer cell lines: DU145, PC3, BT549, HeLa, MDA-MB-231, A549, and MCF-7. Cells growing exponentially in 48-well plates were incubated with different concentrations of compound III for 48 h. The increases in cell numbers were determined by the CyQuant assay and are expressed as a percentage of the increase in control wells with the vehicle (0.1% ethanol). The results are the average+SD from six different wells.
Figure 5:
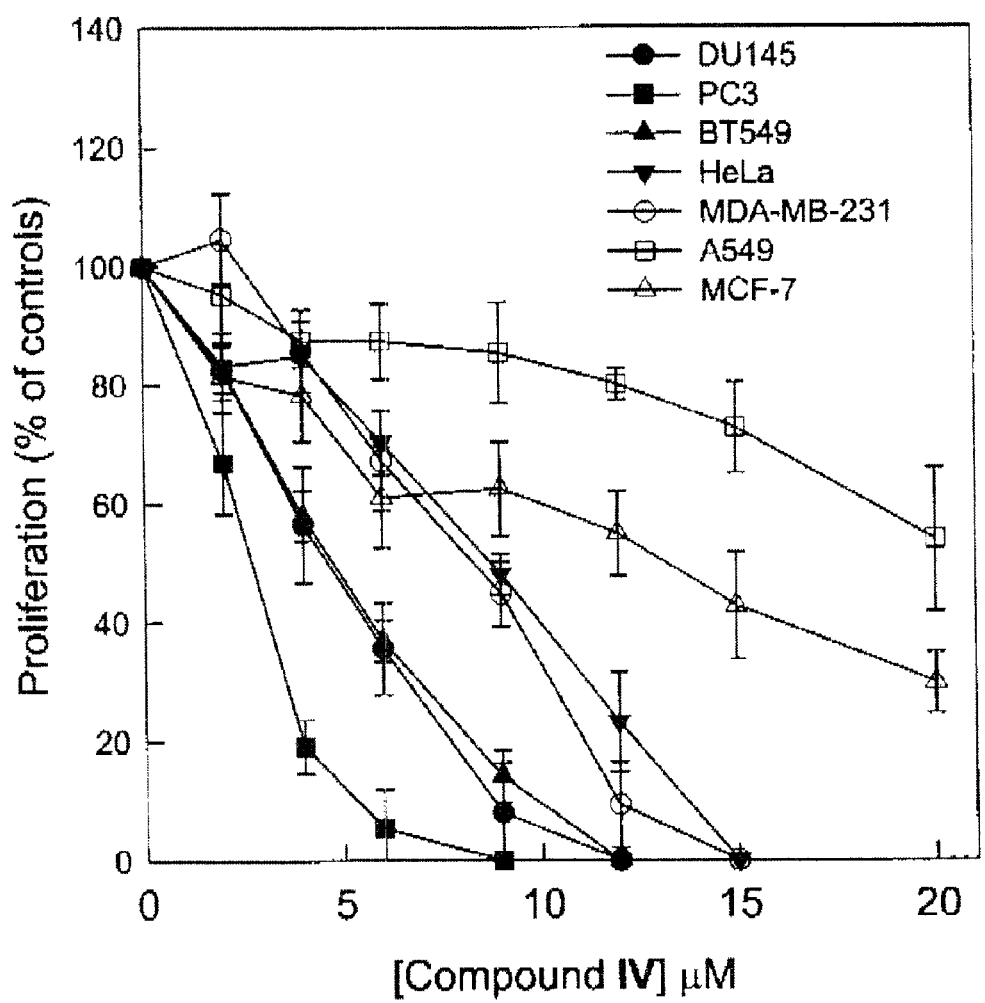
FIG. 5 is a graphical depiction of the results of an antiproliferative evaluation of compound IV against the following cancer cell lines: DU145, PC3, BT549, HeLa, MDA-MB-231, A549, and MCF-7. Cells growing exponentially in 48-well plates were incubated with different concentrations of compound IV for 48 h. The increases in cell numbers were determined by the CyQuant assay and are expressed as a percentage of the increase in control wells with the vehicle (0.1% ethanol). The results are the average+SD from six different wells.
Figure 6:
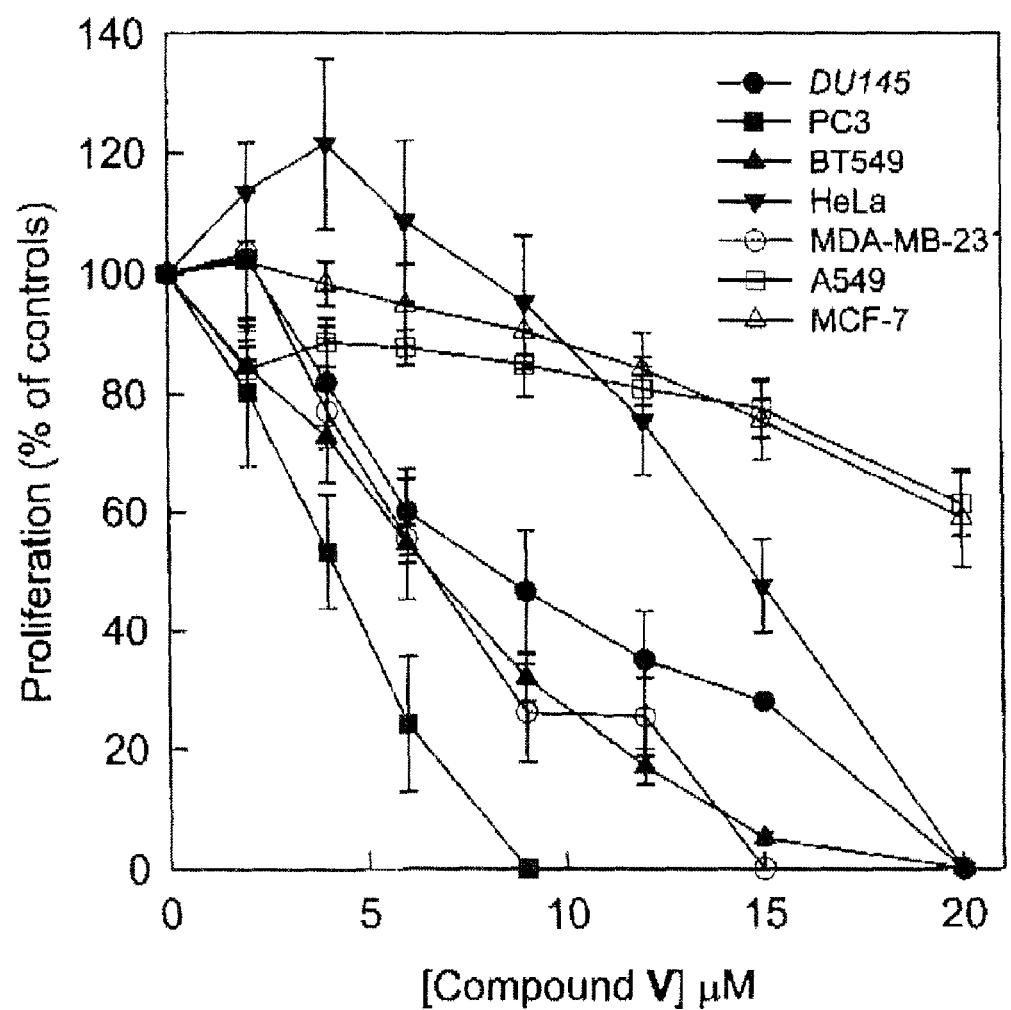
FIG. 6 is a graphical depiction of the results of an antiproliferative evaluation of compound V against the following cancer cell lines: DU145, PC3, BT549, HeLa, MDA-MB-231, A549, and MCF-7. Cells growing exponentially in 48-well plates were incubated with different concentrations of compound V for 48 h. The increases in cell numbers were determined by the CyQuant assay and are expressed as a percentage of the increase in control wells with the vehicle (0.1% ethanol). The results are the average+SD from six different wells.
Figure 9:
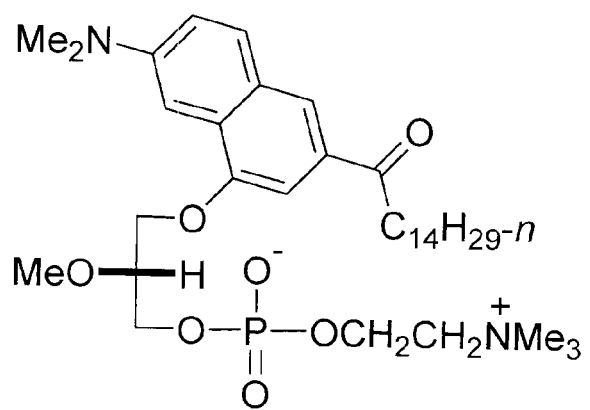
FIG. 9 shows the structure of 1-O-(7-N,N-dimethylamino-3-pentadecanoyl-1-napthyl)-2-O-methyl-sn-glycero-3-phosphocholine.
Figure 10:
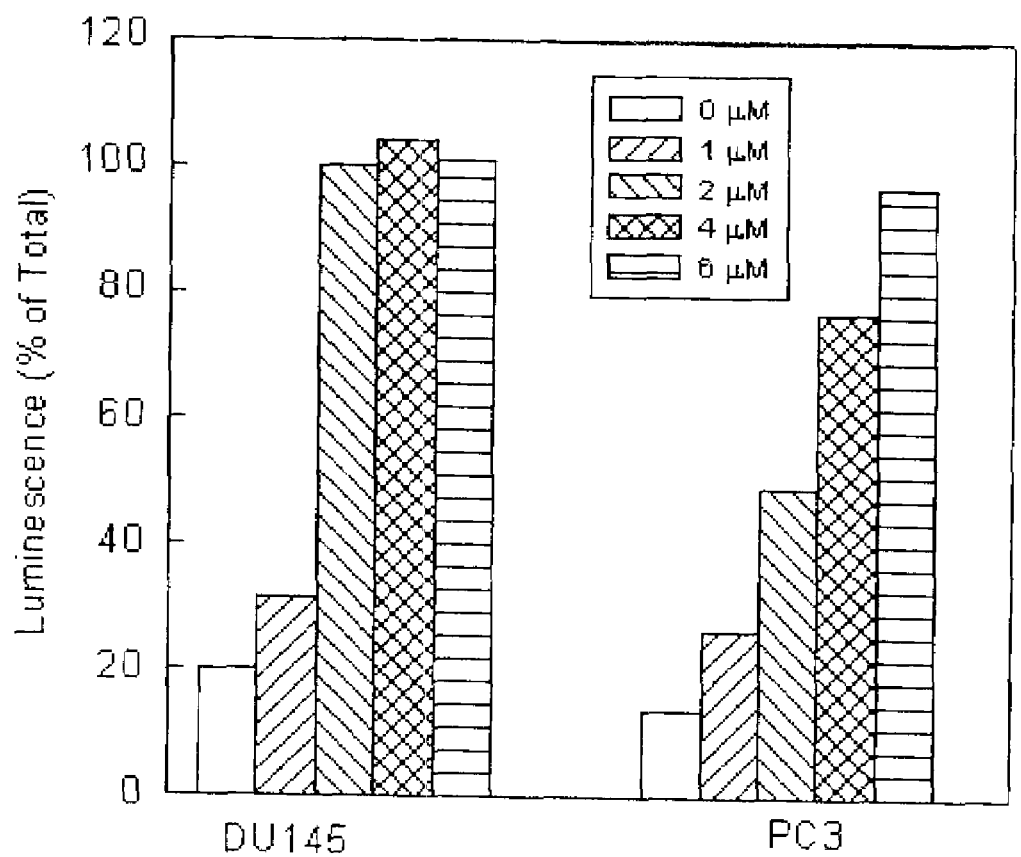
FIG. 10 shows the cytotoxic effect of HB40-6D on DU145 and PC3 cells. Cells were incubated with HB40-6D for 48 h in clear bottom black-coated 96-well plates and the toxicity was determined by the Toxilight assay (Cambrex). 100% lysis of the cells at each concentration was obtained by adding the 100% lysis reagent (Cambrex) to a parallel set of wells.

We screened the compounds against a panel of human cancer cell lines derived from a number of tissues. These were breast (MCF-7, BT549, SKBr3, MDA-MB-231), lung (A549), cervix (HeLa), and prostate (DU145, PC3) cancer cell lines. The results show that the compounds were very active against the cell lines. In some cases, the $IC_{50}$ values were much lower than values reported for ET-18-$OCH_3$, indicative of a greater degree of potency of these new compounds. The most striking observation is that the greatest inhibition of cell growth was found when the two prostate cell lines, DU145 and PC3, were treated with these compounds. Compound I inhibited the proliferation of DU145 cells with an $IC_{50}$ of 1 μM, and was toxic to the cells at a concentration of 2.5 μM. Under similar conditions, ET-18-$OCH_3$ inhibited the proliferation of DU145 cells with an $IC_{50}$ value of 14 μM, and was not toxic even at a concentration of 30 μM (Ashagbley, A. et al., 1966, Anticancer Res. 16, 1813-1818). (The $IC_{50}$ value refers to the concentration at which the proliferation rate of the cells is inhibited by 50% while toxicity refers to the loss of viability of the cells.) When tested against PC3 cells, another hormone-independent prostate cancer cell line derived from the brain, compound I had an $IC_{50}$ value of 1.2 μM, which is similar to that observed in DU145 cells (FIG. 2). These two prostate cancer cell lines are well-known cellular models of the hormone-insensitive stage of prostate cancer (Navone et al., 1999, Cancer Metastasis Rev. 17, 361-371; Sobel and Sadar, 2005, J. Urology 173, 342-359), the most deadly form of the disease that does not respond to current conventional chemotherapy. Because hormone-insensitive prostate cancer cells are highly sensitive to the active compounds described herein, (compounds I, II, and III), we postulate that it may be possible to selectively kill prostate cancer cells with low concentrations without harming other cells in the body. The prostate selectivity observed with compound I was also observed with compounds II and III (Table 1 and FIGS. 3 and 4) and distinguishes these compounds from other antitumor compounds.

In all of our studies, the carbamate- and dicarbamate-containing phospholipid compounds were added to exponentially growing cells, and incubation was for a period of only 48 h. The $IC_{50}$ values of these compounds are impressive compared to the literature data in which established antitumor compounds were added 24 h after cell seeding and drug incubations were for a period of 72 h, with fresh addition of drug media every 24 h (Kreis et al., 1997, Br. J. Urol. 79, 196-202; Budman et al., 2002, Anti-Cancer Drugs 13, 1011-1016).

The results, which are displayed in FIGS. 2-6 and Table 1, are:

The carbamate lipids (compounds I and II) were more active with respect to blocking cancer cell growth than the corresponding dicarbamate lipids (compounds IV and V).

The D stereoisomers (compounds I and IV) were generally more active than the corresponding L isomers (compound II and V) in blocking the growth of the cancer cell lines tested.

Compound III showed the greatest prostate cancer cell selectivity, followed by compounds I and II.

The prostate selectivity was reduced when a second carbamate moiety was introduced into the C2 position of the molecule (as in compounds IV and V).

We have described procedures for the synthesis of ether glycerolipid carbamates (compounds I, II and III) and dicarbamates (compounds IV and V).

We have determined that ether glycerolipid carbamates and dicarbamates, compounds I, II, III, IV, and V, are useful in treating cancers as they possess both antiproliferative and cytotoxic effects.

We have determined that prostate cancer cell lines are particularly sensitive to compounds I, II, and III relative to other cancer cell lines. Therefore, these compounds may provide a means for selectively treating prostate cancer with minimal effects on other cells.

Similarly, 1-O-(7-N, N-dimethylamino-3-pentadecanoyl-1-napthyl)-2-O-methyl-sn-glycero-3-phosphocholine.

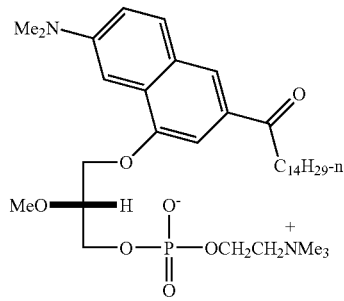

was added to proliferating cells at 0-20 μM for 48 hours, as shown in Table 2. As can be seen, this naphthol-alkyllysophospholipid analog is also highly selective for prostate cancer cells. Specifically, proliferating cells in 48-well plates were incubated with 0-20 μM of the compound for 48 hours. The cell numbers present were determined by the CyQuant™ assay (Invitrogen), and the increase in numbers were expressed relative to the controls receiving only the vehicle (0.1% ethanol).

The present invention also provides pharmaceutical compositions comprising as active ingredients an effective amount of one or more of the above-described carbamate lipids and dicarbamate lipids for use in treating cancer in general and selective treatment of prostate cancer. As used herein, an "effective amount" refers to an amount that is sufficient to inhibit proliferation of cancerous cells, for example, prostate cancer cells. As will be appreciated by one of skill in the art, suitable amounts and concentrations are described herein but will of course depend upon the mode of administration of the pharmaceutical composition, the age, weight and general condition of the patient among other factors.

In some embodiments, the carbamate lipids and dicarbamate lipids, at concentrations or dosages discussed above, may be combined with a pharmaceutically or pharmacologically acceptable carrier, excipient or diluent, either biodegradable or non-biodegradable. Exemplary examples of carriers include, but are by no means limited to, for example, poly (ethylene-vinyl acetate), copolymers of lactic acid and glycolic acid, poly(lactic acid), gelatin, collagen matrices, polysaccharides, poly(D,L lactide), poly(malic acid), poly (caprolactone), celluloses, albumin, starch, casein, dextran, polyesters, ethanol, methacrylate, polyurethane, polyethylene, vinyl polymers, glycols, and mixtures thereof and the like. Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, poiyvinylpyrrolidone, sugars and starches. See, for example, Remington: The Science and Practice of Pharmacy, 1995, Gennaro ed.

As will be apparent to those knowledgeable in the art, specific carriers and carrier combinations known in the art may be selected based on their properties and release characteristics in view of the intended use. Specifically, the carrier may be pH-sensitive, thermo-sensitive, thermo-gelling, arranged for sustained release or a quick burst. In some embodiments, carriers of different classes may be used in combination for multiple effects, for example, a quick burst followed by sustained release.

As discussed herein, the selectivity of the compounds for prostate cancer lines is more surprising than the observed general antitumor properties. The latter is somewhat less surprising because the compound shares some similarities to ET18-OCH$_3$. Nevertheless the bulkiness of the moieties we have inserted at the C-2 position makes the activity surprising since ET-18-OCH$_3$-like compounds generally have a very small moiety at this position.

While not wishing to be bound to a specific hypothesis, the inventors believe that the compounds described herein act to inhibit intracellular pathways that are essential for proliferation and/or activate pathways that lead to cell death via apoptosis or autophagy. The prostate selectivity may result from (A) a greater extent of accumulation of the carbamates, dicarbamates and ureido compounds as a result of greater uptake and/or decreased metabolism in prostate cancer cell lines relative to non prostate cells, (B) a high affinity of the carbamates, dicarbamates, and ureido compounds for receptor-type molecules that are preferentially found in prostate cancer cells, (C) a greater dependence of the prostate cancer cells on pathways perturbed by the compounds for survival and proliferation compared to non-prostate cancer lines."

The procedures for preparing these compounds and the spectral data for characterizing their structures are as follows. Procedures for the Syntheses of Carbamate Phosphonocholine (Compound II) and Dicarbamate Phosphonocholine (Compound V)

As outlined in FIG. 7, the preparation of carbamate phosphonocholine (compound II) and dicarbamate phosphonocholine (compound V) started with 3(S)-1,3-O-benzylidine-1,3,4-butanetriol (2) (Yang et al., 1999). Alkylation of alcohol 2 with sodium hydride and 1-bromohexadecane under phase-transfer conditions gave ether 3 in 91% yield. A benzylidine acetal of the 1,3-dioxane type can undergo ring opening by treatment with N-bromosuccinimide (NBS) to form a O-benzoyl bromohydrin (Hanessian and Plessas, 1969); thus reaction of 3 with NBS in the presence of $BaCO_3$ provided bromohydrin 4 in 87% yield. Arbuzov reaction of bromohydrin 4 with $P(OEt)_3$ at 150° C. gave benzoyl phosphonate 5 in 79% yield. Base-induced hydrolysis of the benzoyl group of phosphonate 5 provided hydroxyphosphonate 6 in 86% yield. During the deprotection of the benzoate group by methanolysis the ethyl groups in phosphonate 5 were converted to methyl groups by transesterification. Hydroxyphosphonate 6 was reacted with methyl isocyanate, which was generated in situ by the reaction of methyl iodide with KNCO in tetrahydrofuran/N,N-dimethylformamide (THF/DMF) (10:1 v/v), furnishing a mixture of carbamate 7 and carbamate 8 in 11% and 53% yields, respectively. When the amount of DMF was increased, the rate of carbamate formation was faster but the yield of carbamate 7 decreased. The methyl groups in the phosphonate ester were removed by treatment of 7 or 8 with trimethylsilyl bromide in $CH_2Cl_2$, and a choline group was introduced by coupling of the resulting phosphonic acid with choline tosylate promoted by trichloroacetonitrile in pyridine.

Procedures for the Syntheses of Carbamate Phosphonocholine (Compound I) and Dicarbamate Phosphonocholine (Compound IV).

The enantiomer of compound II (compound I) and the enantiomer of compound V (compound IV) were prepared starting from 3(R)-1,3-O-benzylidine-1,3,4-butanetriol by using procedures similar to those described above.

Detailed Experimental Procedures for the Preparations of Compounds I, II, IV, and V.

General Information. $^1H$ and $^{13}C$ NMR spectra were recorded at 400 and 100 MHz, respectively, and were referenced to the residual chloroform at δ 7.24 ($^1H$) and δ 77.00 ppm ($^{13}C$). Optical rotations were measured in a cell of 1-dm pathlength on a digital polarimeter. TLC was carried out on aluminum-backed silica gel GF plates (250-μm thickness), and the compounds were visualized by charring with 10% sulfuric acid in ethanol and/or short wavelength UV light. For flash chromatography, silica gel 60 (230400 ASTM mesh) was used. THF was distilled from sodium and benzophenone before use. Pyridine, DMF, 1,2-dichlorethane, $EtN(Pr-i)_2$, and $CH_2Cl_2$ were dried over $CaH_2$.

Preparation of (3S)-4-O-hexadecyl-1,3-O-benzylidine-1,3,4-butanetriol (3). To a suspension of 1.60 g (40.0 mmol) of NaH (60% in white oil, washed twice with dry hexane) in 100 mL of dry THF was added 3.89 g (20.0 mmol) of (3S)-1,3-O-benzylidine-1,3,4-butanetriol (2) in 20 mL of THF at 0° C. After the evolution of hydrogen had stopped, 6.2 mL (20.2 mmol) of 1-bromohexadecane and 0.67 g (2.0 mmol) of $n-Bu_4NBr$ were added. The mixture was stirred for 24 h at room temperature, and then the reaction was quenched with 10 mL of MeOH. The volatile solvents were removed under reduced pressure, and the residue was diluted with 200 mL of $Et_2O$ and washed with water. The organic layer was dried over $Na_2SO_4$ and concentrated under reduced pressure to give a residue. The residue was purified by column chromatography on silica gel (elution with hexane/EtOAc 25:1), affording 7.62 g (91%) of (3S)-4-O-hexadecyl-1,3-O-benzylidine-1,3,4-butanediol (3) (Yang et al., 1999, Org. Lett. 1, 2149-2151) as a white solid; mp 54-55° C.; $^1H$ NMR ($CDCl_3$) δ 0.88 (t, 3H, J=6.6 Hz), 1.25 (br s, 26H), 1.54-1.60 (m, 3H), 1.80-1.91 (m, 1H), 3.44-3.52 (m, 3H), 3.62 (dd, 1H, J=5.8, 10.3 Hz), 3.95-4.01 (m, 1H), 4.01-4.09 (m, 1H), 4.29 (dd, 1H, J=4.1, 11.4Hz), 5.53 (s, 1H), 7.31-7.38 (m, 3H), 7.49 (dd, 2H, J=1.6, 7.9 Hz); $^{13}C$ NMR ($CDCl_3$) δ 14.1, 22.7, 26.1, 28.3, 29.3, 29.5, 29.6, 29.7, 30.9, 31.9, 66.9, 71.9, 73.7, 76.3, 101.2, 126.1, 128.2, 128.7, 129.0, 129.7, 138.6; MS (electrospray) $MH^+$ m/z calcd for $C_{27}H_{47}O_3$ 419.35, found 419.2.

Preparation of 3(R)-4-O-hexadecyl-1,3-O-benzylidine-1,3,4-butanetriol. The enantiomer of 3 was prepared in 90% yield from (3R)-1,3-O-benzylidine-1,3,4-butanetriol by the procedure described above.

Preparation of 3(S)-benzoyl-4-hexadecyloxy-1-bromobutane (4). A mixture of 5.19 g (12.4 mmol) of (3S)-4-O-hexadecyl-1,3-O-benzylidine-1,3,4-butanediol (3), 2.65 g (14.9 mmol) of NBS, and 1.10 g (5.57 mmol) of $BaCO_3$ in 100 mL of $CCl_4$ (or $ClCH_2CH_2Cl$) was heated at reflux for 4 h. The reaction mixture was passed through a pad of silica gel, which was rinsed with 100 mL of hexane/EtOAc (10:1). The filtrate was concentrated to give a residue, which was purified by column chromatography on silica gel (elution with hexane/EtOAc 25:1) to provide 5.36 g (87%) of bromide 4 as a pale yellow oil; $[α]^{25}_D$ −24.90 (c 6.7, $CHCl_3$); $^1H$ NMR ($CDCl_3$) δ 0.88 (t, 3H, J=6.6 Hz), 1.26 (br s, 26H), 1.50-1.56 (m, 2H), 2.31-2.41 (m, 2H), 3.42-3.50 (m, 4H), 3.62-3.65 (m, 2H), 5.35-5.41 (m, 1H), 7.42-7.46 (m, 2H), 7.54-7.59 (m, 1H), 8.05 (dd, 2H, J=1.4, 8.4 Hz); $^{13}C$ NMR ($CDCl_3$) δ 14.1, 22.6, 26.0, 28.7, 29.3, 29.4, 29.5, 29.6, 31.9, 34.5, 71.2, 71.67, 71.72, 128.3, 129.6, 130.0, 133.0, 165.9; MS (electrospray) MH+ m/z calcd for $C_{27}H_{46}BrO_3$ 497.26, found 497.2.

Preparation of 3(R)-benzoyl-4-hexadecyloxy-1-bromobutane. The enantiomer of bromide 4 was prepared in 85% yield from 3(R)-4-O-hexadecyl-1,3-O-benzylidine-1,3,4-butanediol by the procedure described above; $[α]^{25}_D$ +20.5° (c 6.9, $CHCl_3$).

Preparation of diethyl 3(S)-benzoyl-4-hexadecyloxy-1-butanephosphonate (5). A solution of 4.98 g (10.0 mmol) of bromide 4 in 25 mL (150 mmol) of triethyl phosphite [(EtO)$_3$P] was heated at 150° C. (oil bath temperature) overnight. After the excess of $(EtO)_3P$ was removed by using a stream of air, the residue was purified by column chromatography on silica gel (elution with $CHCl_3$/MeOH 25:1) to give 4.39 g (79%) of benzoyl phosphonate 5 as a colorless oil; $[α]^{25}_D$ −6.88° (c 5.8, $CHCl_3$); $^1H$ NMR ($CDCl_3$) δ 0.88 (t, 3H, J=6.7 Hz), 1.26 (br s, 26H), 1.28-1.33 (m, 6H), 1.70-2.00 (m, 2H), 3.43-3.62 (m, 4H), 4.06-4.12 (m, 4H), 5.23-5.27 (m, 1H), 7.42-7.46 (m, 2H), 7.54-7.59 (m, 1H), 8.04 (d, 2H, J=7.0 Hz); $^{13}C$ NMR ($CDCl_3$) δ 14.1, 16.4 (d, J=5.8 Hz), 22.2 (d, J=143.2 Hz), 22.6, 24.3 (d, J=4.0 Hz), 29.3, 29.4, 29.6, 29.7, 31.9, 61.6, 71.3, 71.7, 72.8 (d, J=18.1 Hz), 127.7, 128.3, 129.6, 130.1, 133.0, 166.0; MS (electrospray) $MH^+$ m/z calcd for $C_{31}H_{56}O_6P$ 555.39, found 555.3.

Preparation of diethyl 3(R)-benzoyl-4-hexadecyloxy-1-butanephosphonate. The enantiomer of benzoyl phosphonate 5 was prepared in 80% yield from 3(R)-benzoyl-4-hexadecyloxy-1-bromobutane by the procedure descried above; $[\alpha]^{25}_D$ +6.71° (c 6.0, CHCl$_3$).

Preparation of dimethyl 4-hexadecyloxy-3(S)-hydroxy-1-butanephosphonate (6). To 100 mL of dry MeOH was added 0.18 g (7.83 mmol) of sodium metal. After the sodium metal had completely disappeared, a solution of 3.91 g (7.05 mmol) of benzoyl phosphonate 5 in 10 mL of dry MeOH was added. After the mixture was stirred overnight, the reaction was quenched by addition of 500 μL (8.73 mmol) of AcOH and then concentrated under reduced pressure to give a residue. The residue was purified by column chromatography on silica gel (elution with CHCl$_3$/MeOH 10:1) to provide 2.56 g (86%) of hydroxy phosphonate 6 as a colorless oil; $[\alpha]^{25}_D$ -5.20° (c 5.0, C$_6$H$_6$); $^1$H NMR (CDCl$_3$) δ 0.88 (t, 3H, J=6.8 Hz), 1.26 (br s, 26H), 1.54-1.58 (m, 2H), 1.70-1.90 (m, 4H), 2.78 (br s, 1H), 3.29 (dd, 1H, J=7.1, 9.4 Hz), 3.40-3.48 (m, 3H), 3.74 (d, 6H, J=10.8 Hz), 3.70-3.85 (m, 1H); $^{13}$C NMR (CDCl$_3$) δ 14.0, 20.7 (d, J=142.1 Hz), 22.6, 26.0, 26.1 (d, J=4.7 Hz), 29.3, 29.4, 29.5, 29.6, 31.9, 52.3, 69.8 (d, J=14.8 Hz), 71.6, 74.4; MS (electrospray) MH$^+$ m/z calcd for C$_{22}$H$_{48}$O$_5$P 423.3, found 423.3.

Preparation of dimethyl 4-hexadecyloxy-3(R)-hydroxy-1-butanephosphonate. The enantiomer of hydroxy phosphonate 6 was prepared in 88% yield from diethyl 3(R)-benzoyl-4-hexadecyloxy-1-butanephosphonate by the procedure described above; $[\alpha]^{25}_D$ +5.22° (c 5.1, C$_6$H$_6$).

Preparation of dimethyl 4-hexadecyloxy-3(S)—N-methylcarbamoyl-1-butanephosphonate (7) and dimethyl 4-hexadecyloxy-3(S)-[N—(N'-methylcarbamoyl)-N-methylcarbamoyl]-1-butanephosphonate (8). To a mixture of 8.11 g (100 mmol) of potassium cyanate, 3.22 g (10 mmol) of n-Bu$_4$NBr, and 2.12 g (5.02 mmol) of hydroxy phosphonate 6 in 25 mL of 10:1 THF/DMF were added 3.2 mL (51.4 mmol) of methyl iodide and 1.8 mL (10.4 mmol) of (i-Pr)$_2$NEt. The mixture was stirred until hydroxy phosphonate 6 was completely consumed, as indicated by TLC. The reaction mixture was diluted with CHCl$_3$ and washed with brine solution. The organic layer was dried over Na$_2$SO$_4$ and concentrated. The product was purified by column chromatography on silica gel (elution with CHCl$_3$, and then with 100:1 (v/v) CHCl$_3$/MeOH, 50:1 (v/v) CHCl$_3$/MeOH, 25:1 (v/v) CHCl$_3$/MeOH) to give 265 mg (11%) of carbamoyl phosphonate 7 and 1.43 g (53%) of dicarbamoyl phosphonate 8 as colorless oils: Spectral data for compound 7: $[\alpha]^{25}_D$ -5.820 (c 5.5, CHCl$_3$); $^1$H NMR (CDCl$_3$) δ 0.88 (t, 3H, J=6.4 Hz), 1.26 (br s, 26H), 1.48-1.62 (m, 2H), 1.15-2.00 (m, 4H), 2.87 (d, 3H, J=4.8 Hz), 3.25-3.50 (m, 6H), 3.75 (d, 6H, J=10.8 Hz), 4.90-5.00 (m, 1H), 7.60-7.70 (br s, 1H); $^{13}$C NMR (CDCl$_3$) δ 14.1, 20.7 (d, J=151 Hz), 22.6, 24.0 (d, J=5.0 Hz), 26.0, 26.1, 26.4, 29.3, 29.4, 29.5, 29.6, 31.9, 52.4, 67.8, 74.4 (d, J=6.0 Hz), 153.7; $^{31}$P NMR (CDCl$_3$) δ 35.5; MS (electrospray) MH$^+$ m/z calcd for C$_{24}$H$_{51}$NO$_6$P 480.3, found 480.3. Spectral data for compound 8: $[\alpha]^{25}_D$ -4.700 (c 5.6, CHCl$_3$); $^1$H NMR (CDCl$_3$) δ 0.88 (t, 3H, J=6.0 Hz), 1.25 (br s, 26H), 1.50-1.62 (m, 2H), 1.75-1.86 (m, 2H), 1.90-2.10 (m, 2H), 2.87 (d, 3H, J=4.4 Hz), 3.22 (s, 3H), 3.42-3.52 (m, 4H), 3.51 (t, 2H, J=5.2 Hz), 3.75 (d, 6H, J=10.8 Hz), 4.90-5.00 (m, 1H), 8.40-8.50 (br s, 1H); $^{13}$C NMR (CDCl$_3$) δ 14.1, 20.7 (d, J=143 Hz), 22.4, 24.0 (d, J=4.3 Hz), 26.0, 27.1, 29.3, 29.4, 29.5, 29.6, 30.7, 31.9, 52.5, 71.1, 71.7, 75.0 (d J=17.5 Hz), 155.2, 155.9; $^{31}$P NMR (CDCl$_3$) δ 33.6; MS (electrospray) MH$^+$ m/z calcd for C$_{26}$H$_{54}$N$_2$O$_7$P 537.37, found 537.3.

Preparation of dimethyl 4-hexadecyloxy-3(R)—N-methylcarbamoyl-1-butanephosphonate dimethyl and 4-hexadecyloxy-3(R)-[N—(N'-methylcarbamoyl)-N-methylcarbamoyl]-1-butanephosphonate. The enantiomers of carbamoyl phosphonate 7 and dicarbamoyl phosphonate 8 were prepared in 12% and 50% yields, respectively, from 4-hexadecyloxy-3(R)-hydroxy-1-butanephosphonate by the procedure described above. Spectral data for the enantiomer of 7: $[\alpha]^{25}_D$ +5.49° (c 5.6, CHCl$_3$); MS (electrospray) MH$^+$ m/z calcd for C$_{24}$H$_{51}$NO$_6$P 480.3, found 480.3. Spectral data for the enantiomer of 8: $[\alpha]^{25}_D$ +4.55° (c 5.7, CHCl$_3$); MS (electrospray) MH$^+$ m/z calcd for C$_{26}$H$_{54}$N$_2$O$_7$P 537.37, found 537.3.

Preparation of 2'-(trimethylammonio)ethyl 4-hexadecyloxy-3(S)—N-methylcarbamoyl-1-butane-phosphonate (Compound II). To a solution of 512 mg (1.07 mmol) of carbamoyl phosphonate 7 in 25 mL of CH$_2$Cl$_2$ was added 500 μL (3.79 mmol) of trimethylsilyl bromide. After the mixture was allowed to stand overnight at room temperature, the volatile materials were removed under reduced pressure to give a residue. To the residue was added 1.45 g (3.01 mmol) of choline tosylate, and the mixture was dried overnight under high vacuum. After the dry mixture was dissolved in 50 mL of pyridine, 1.5 mL (15.0 mmol) of trichloroacetonitrile was added, and the reaction mixture was heated for 48 h at 50° C. (oil bath temperature). On removal of most of the pyridine by rotary evaporation, a brown residue was formed, which was dissolved in THF/H$_2$O (10 mL, 9:1 v/v) and passed through a column of TMD-8 resin (previously equilibrated with the same solvent mixture). The product was purified by silica gel chromatography (elution with CHCl$_3$/MeOH/H$_2$O 65:25:4 v/v/v). The fractions containing the product (as identified by TLC) were pooled and concentrated under reduced pressure. The residue was dissolved in CHCl$_3$ (15-25 mL) and passed through a Cameo filter three times to remove the suspended silica gel. The filtrate was concentrated to give a residue, which was lyophilized from benzene to afford 395 mg (69%) of phosphonate 1a as a white powder; $[\alpha]^{25}_D$ -2.53° (c 0.21, CHCl$_3$/MeOH 1:1); $^1$H NMR (CDCl$_3$/CD$_3$OD) δ 0.89 (t, 3H, J=6.4 Hz), 1.26 (br s, 26H), 1.32-1.35 (m, 2H), 1.44-1.62 (m, 4H), 1.86-1.95 (m, 2H), 2.86 (d, 3H, J=4.8 Hz), 3.24 (s, 9H), 3.30-3.70 (m, 8H), 4.90-5.00 (m, 1H); $^{13}$C NMR (CDCl$_3$) δ 14.1, 20.7 (d, J=143 Hz), 22.6, 25.1 (d, J=4.1 Hz), 26.0, 26.1, 26.4, 29.3, 29.4, 29.5, 29.6, 31.9, 56.5 (d, J=4.7 Hz), 65.8, 70.6 (d, J=5.8 Hz), 75.4, 75.5, 74.9, 153.7; MS (electrospray) M$^+$ m/z calcd for C$_{27}$H$_{58}$N$_2$O$_6$P 537.37, found 537.4.

Preparation of 2'-(trimethylammonio)ethyl 4-hexadecyloxy-3(R)—N-methylcarbamoyl-1-butanephosphonate (Compound I). The enantiomer of compound II was prepared in 66% yield from dimethyl 4-hexadecyloxy-3(R)—N-methylcarbamoyl-1-butanephosphonate by the procedure described above; $[\alpha]^{25}$D +2.44° (c 0.21, CHCl$_3$/MeOH 1:1); MS (electrospray) M$^+$ m/z calcd for C$_{27}$H$_{58}$N$_2$O$_6$P 537.37, found 537.3.

Preparation of 2'-(trimethylammonio)ethyl 4-hexadecyloxy-3(S)-[N—(N'-methylcarbamoyl)-N-methylcarbamoyl]-1-butanephosphonate (Compound V). Compound V was prepared in 71% yield from dimethyl 4-hexadecyloxy-3(S)-[N—(N'-methylcarbamoyl)-N-methylcarbamoyl]-1-butanephosphonate by the procedure described above; $[\alpha]^{25}_D$ -2.07° (c 0.23, CHCl$_3$/MeOH 1:1); $^1$H NMR (CDCl$_3$/CD$_3$OD) δ 0.89 (t, 3H, J=6.4 Hz), 1.26 (br s, 26H), 1.44-1.62 (m, 4H), 1.86-1.95 (m, 4H), 2.87 (d, 3H, J=4.0 Hz), 3.24 (s, 3H), 3.26 (s, 9H), 3.35-3.70 (m, 8H), 4.95-5.05 (m, 1H); $^{13}$C NMR (CDCl$_3$) δ 14.1, 20.7 (d, J=143 Hz), 22.6, 25.1 (d, J=4.1 Hz), 26.0, 26.1, 26.4, 29.3, 29.4, 29.5, 29.6, 31.9, 56.5 (d, J=4.7 Hz), 65.8, 70.6 (d, J=5.8 Hz), 75.4, 75.5, 74.8, 155.4, 156.1; MS (electrospray) M+ m/z calcd for $C_{29}H_{61}N_3O_7P$ 594.4, found 594.3.

Preparation of 2'-(trimethylammonio)ethyl 4-hexadecyloxy-3(R)-[N—(N'-methylcarbamoyl)-N-methylcarbamoyl]-1-butanephosphonate (Compound IV). The enantiomer of compound V was prepared in 68% yield from dimethyl 4-hexadecyloxy-3(R)-[N—(N'-methylcarbamoyl)-N-methylcarbamoyl]-1-butanephosphonate by the procedure described above; $[\alpha]^{25}_D$ +1.98° (c 0.21, $CHCl_3$/MeOH 1:1); MS (electrospray) $M^+$ m/z calcd for $C_{29}H_{61}N_3O_7P$ 594.4, found 594.3.

References cited in the experimental procedures above:
1. Yang, G.; Franck, R. W.; Byun, H.-S.; Bittman, R.; Samadder, P.; Arthur, G. Org. Lett. 1999, 1, 2149-2151.
2. Hanessian, S.; Plessas, N. R. J. Org. Chem. 1969, 34, 1035-1044.

Procedures for the Synthesis of Carbamate Phosphorylcholine (Compound III)

As depicted in FIG. 8, the preparation of carbamate phosphorylcholine (compound II) started with 3-O-hexadecyl-sn-glycerol (2) (van Boeckel et al., 1982). Regioselective and stereospecific azidation of glycerol 2 with azidotrimethylsilane ($Me_3SiN_3$) under Mitsunobu conditions gave azido alcohol 3 in 76% yield (He et al., 1999). Insertion of the phosphocholine head group into alcohol 3 provided 2-azidophosphorylcholine 5 in 69% overall yield by the following sequence of reactions: phosphorylation of alcohol 3 with 2-chloro-2-oxo-1,3,2-dioxaphospholane, ring opening of phospholane intermediate 4 with trimethylsilyl bromide, and quaternization of the resulting ring-opened product with aqueous trimethylamine. Finally, reduction of the azido group of 5 by catalytic hydrogenation followed by reaction of amine 6 with methyl chloroformate furnished carbamate phosphorylcholine (compound III) (85% overall yield from 5).

Detailed Experimental Procedures for the Preparation of Compound III.

2(S)-Azido-3-O-hexadecyl-1,3-propanediol (3). To a solution of 3.17 g (10.0 mmol) of 3-O-hexadecyl-sn-glycerol (2) and 3.42 g (13.0 mmol) of $Ph_3P$ in 180 mL of $CH_2Cl_2$ was added 3.2 mL (15 mmol) of diisopropyl azodicarboxylate (DIAD) at 0° C. After the mixture was stirred for 3 h under nitrogen, $Me_3SiN_3$ was added. The mixture was stirred at the same temperature for 3 h, and then at room temperature until glycerol 2 had reacted completely. The reaction mixture was concentrated to give a yellow residue, which was dissolved in a minimum volume of $CH_2Cl_2$ and passed through a pad of silica gel in a sintered glass funnel. The pad was rinsed with hexane/EtOAc (50:1) until the excess yellow DIAD began to elute. After concentration of the eluted silyloxy azide, the residue was dissolved in 30 mL of THF and treated with 25 mL of a 1 M (n-Bu)$_4$NF solution in THF. The mixture was stirred at room temperature until all of the silyloxy azides were consumed completely, and then was diluted with 250 mL of $Et_2O$ and washed with water and brine. The organic layer was separated, dried over $Na_2SO_4$, and concentrated The crude product was purified by column chromatography on silica gel (elution first 150 mL of 50:1 hexane/EtOAc and then with 6:1 hexane/EtOAc) to give 2.60 (76%) of azido alcohol 3 as a white solid: mp 37-39° C., (Ponpipom and Bugianesi, 1984). 38-29° C.; $[\alpha]^{25}_D$ +14.50 (c 1.0, $CHCl_3$), (Ponpipom and Bugianesi 1984. $[\alpha]^{27}_D$ +14.1° (c 1.0, $CHCl_3$); $^1$H NMR ($CDCl_3$) δ 0.88 (t, 3H, J=6.4 Hz), 1.26 (s, 26H), 1.52-1.62 (m, 2H), 2.19 (br s, 1H), 3.47 (t, 2H, J=6.8 Hz), 3.55-3.63 (m, 4H), 3.65-3.80 (m, 1H); $^{13}$C NMR ($CDCl_3$) δ 14.1, 22.7, 26.0, 29.3, 29.4, 29.5, 29.6, 29.7, 31.9, 62.3, 63.0, 70.9, 71.9.

Preparation of 2'-(trimethylammonio)ethyl 2(S)-azido-3-hexadecyloxypropanephosphate (5)

To a solution of 342 mg (1.00 mmol) of 2(S)-azido-3-O-hexadecyl-1,3-propanediol (3) and 390 mg (3.02 mmol) of $EtN(Pr-i)_2$ in 20 mL of $CH_2Cl_2$ was added 250 μL (2.72 mmol) of 2-chloro-1,3,2-dioxaphospholane-2-oxide at 0° C. After azido alcohol 3 was consumed completely, $Me_3SiBr$ (1.0 mL, 7.6 mmol) was added at 0° C. to carry out the ring-opening reaction of the phospholane. After the mixture was stirred for 2 h at room temperature, the volatile material was removed under reduced pressure to give a residue. The residue was dissolved in 40 mL of 0.9:1.5:1.5 (v/v/v) $CHCl_3$/MeCN/2-PrOH and treated with 40 mL of 40% aqueous $Me_3N$ solution for 2 days at room temperature. After concentration under reduced pressure, the residue was purified by column chromatography on silica gel (elution with $CHCl_3$/MeOH/$H_2O$ 65:25:4 v/v/v) to give 350 mg (69%) of azidophosphorylcholine 5 as a white solid: $[\alpha]^{25}_D$ −4.3° (c 0.11, $CHCl_3$), $[\alpha]^{25}_D$ −4.5° (c 1.0, $CHCl_3$); $^1$H NMR ($CDCl_3$/$CD_3OD$) δ 0.88 (t, 3H, J=6.4 Hz), 1.26 (s, 26H), 1.50-1.60 (m, 2H), 3.30 (s, 9H), 3.43-3.65 (m, 4H), 3.25-3.50 (m, 3H), 3.90-4.10 (m, 2H), 4.35-4.45 (m, 2H); $^{13}$C NMR ($CDCl_3$/$CD_3OD$) δ 13.6, 22.3, 25.6, 29.0, 29.1, 29.2, 29.3, 31.6, 44.4, 53.9, 59.5 (d, J=5.0 Hz), 60.7 (d, J=7.0 Hz), 65.7 (d, J=5.0 Hz), 69.6, 71.7; $^{31}$P NMR ($CDCl_3$/$CD_3OD$) δ-2.03.

Preparation of 2'-(trimethylammonio)ethyl 2(S)—(N-methoxycarbonylamido)-3-hexadecyloxypropanephosphate (III)

A mixture of 102 mg (0.20 mmol) of azidophosphorylcholine 5 and Pd/C (30 mg) in EtOH was stirred overnight under hydrogen atmosphere. After the catalyst was removed by filtration, the filtrate was concentrated under reduced pressure to give crude amine 6. To a solution of vacuum-dried amine 6 in 10 mL of alcohol-free $CHCl_3$ were added 60 μL (0.44 mmol) of $Et_3N$ and 30 μL (0.39 mmol) of methyl chloroformate at 0° C. The mixture was stirred overnight at room temperature and then concentrated under reduced pressure to give a residue. The residue was purified by column chromatography on silica gel (elution with $CHCl_3$/MeOH/$H_2O$ 65:25:4 v/v/v) to give 93 mg (85%) of carbamate phosphorylcholine III as a white solid: $[\alpha]^{25}_D$ −3.9° (c 0.10, $CHCl_3$); $^1$H NMR ($CDCl_3$) δ 0.88 (t, 3H, J=6.4 Hz), 1.26 (s, 26H), 1.50-1.60 (m, 2H), 3.43 (s, 9H), 3.40-3.75 (m, 4H), 3.67 (s, 3H), 3.90-4.30 (m, 5H), 4.60-4.80 (m, 2H), 6.51 (brs, 1H); $^{31}$P NMR ($CDCl_3$) δ-2.61.

References for the experimental procedures for preparation of compound III:
1. van Boeckel, C. A. A.; van del Marel, G. A.; Westerduin, P.; van Boom, J. H. Synthesis 1982, 399-402.
2. He, L.; Wanunu, M.; Byun, H.-S.; Bittman, R. J. Org. Chem. 1999, 64, 6049-6055.
3. Ponpipom, M. M.; Bugianesi, R. L. Chem. Phys. Lipids 1984, 35, 29-37.

Synthesis of Ureido Analog.

The ureido analog (VI) was made as follows: diethyl azodicarboxylate (DEAD) was added dropwise to a solution of the hydroxy phosphonocholine, $PPh_3$, and $HN_3$ in toluene at 0° C., with stirring for 30 min. After hexane was added, the mixture was filtered through a silica gel pad to yield the crude azide, which was dissolved in $Et_2O$ and reduced to the amine with lithium aluminum hydride at 0° C. After quenching of the reaction with water and filtration through Celite, the crude amine was obtained. The amine was dissolved in 2-propanol, and a solution of trimethylsilyl isocyanate in 2-propanol was added at room temperature. After 4 h of stirring, the mixture was concentrated under vacuum and the ureido-phosphonate was obtained by silica gel chromatography.

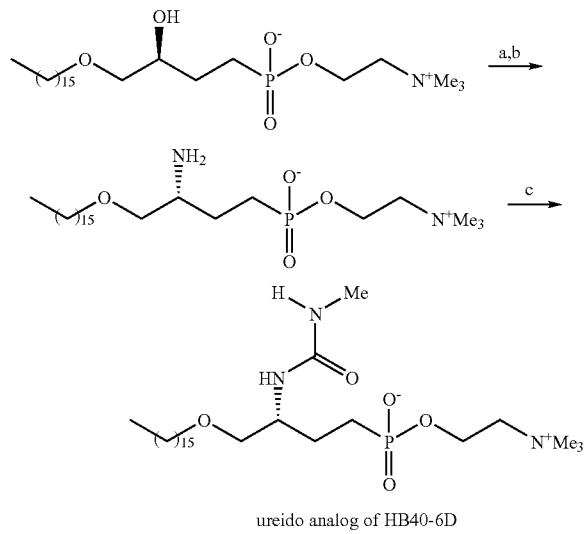

ureido analog of HB40-6D

Key: (a) HN₃, DEAD, PPh₃, toluene, 0° C.; (b) LiAlH₄, Et₂O, 0° C.; (c) TMSNCO, 2-PrOH, rt.

Schemes for the Synthesis of Ureido-C-galactoside (VII) and Ureido-C-aminogalactoside (VIII)

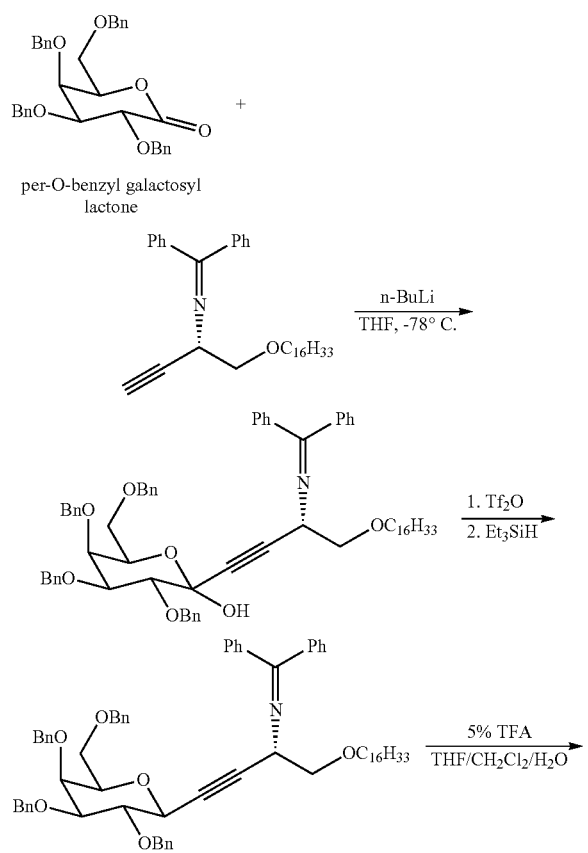

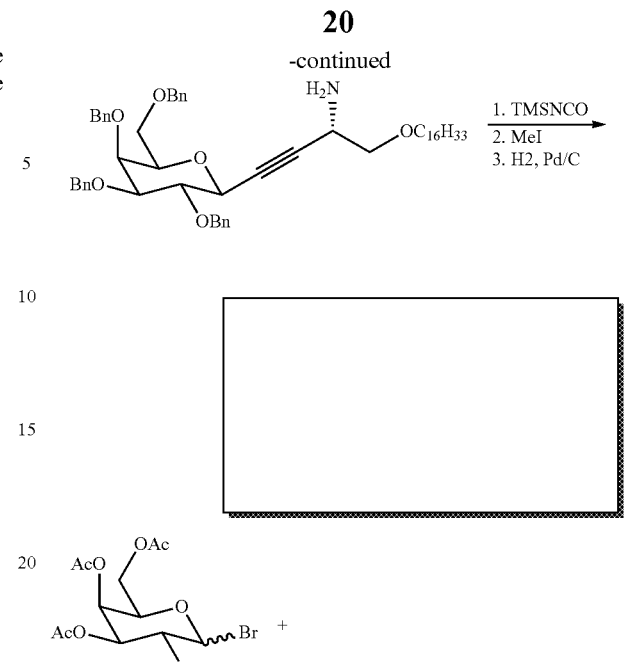

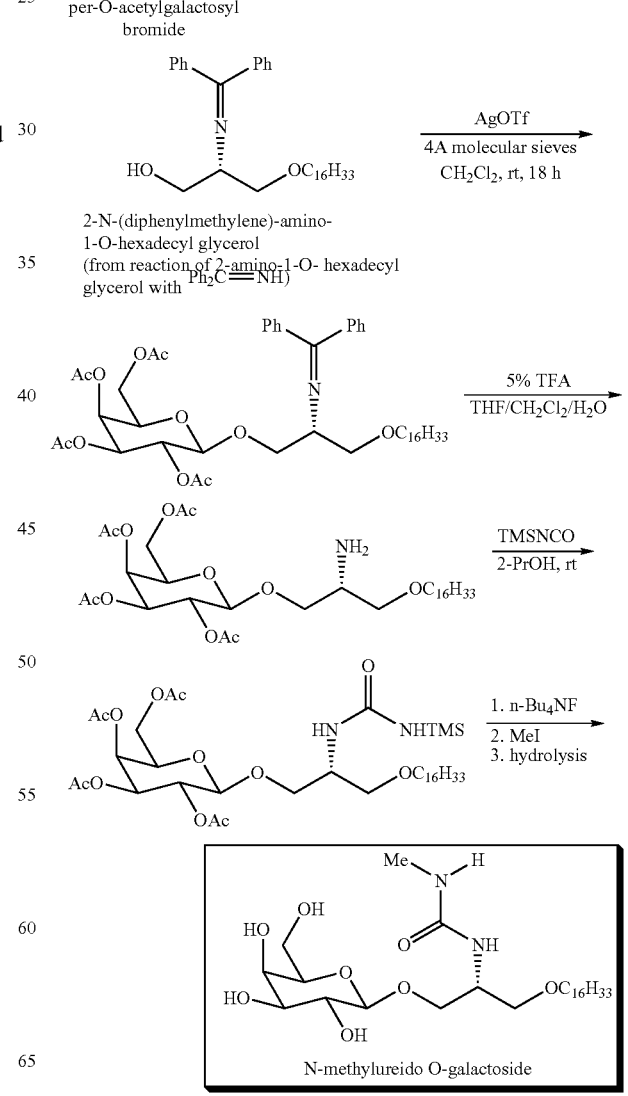

N-methylureido O-galactoside

-continued

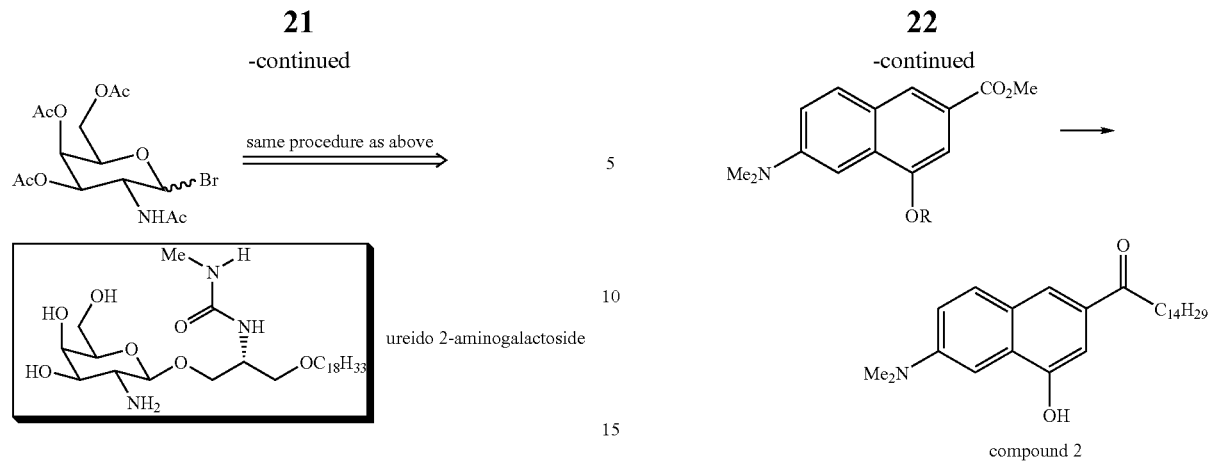

ureido 2-aminogalactoside

Provided below is a reaction scheme for the synthesis of Naphthol Carbamoyl Phosphonocholine derivative. 1-O-tert-Butyidimethylsilyl-2-(O-4'-methoxybenzyl)-3-O-tert-butyl-diphenylsilyl-sn-glycerol was converted to (S)-3-iodo-2-(O-4'-methoxybenzyl)-1-O-tert-butyldiphenylsilyl-propane-1,2-diol via selective desilylation of the tert-butyidimethylsilyl group, followed by tosylation of the liberated primary hydroxyl group and $S_N2$ reaction with iodide ion. Coupling of the iodo glyceride with the naphthol derivative, compound 2 (which was synthesized from 4-(dimethylamino)benzaldehyde as outlined in the accompanying scheme), afforded compound 1. Compound 1 was converted to the naphthol phosphocholine product by the following sequence of reactions: removal of the 4'-methoxybenzyl group, insertion of the carbamoyl moiety, desilylation, and installation of the phosphocholine moiety.

Synthesis of Naphthol Carbamoyl Phosphocholine Derivative

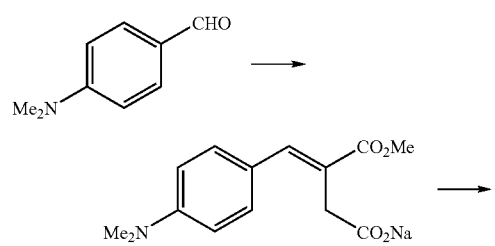

Synthesis of cpd. 2:

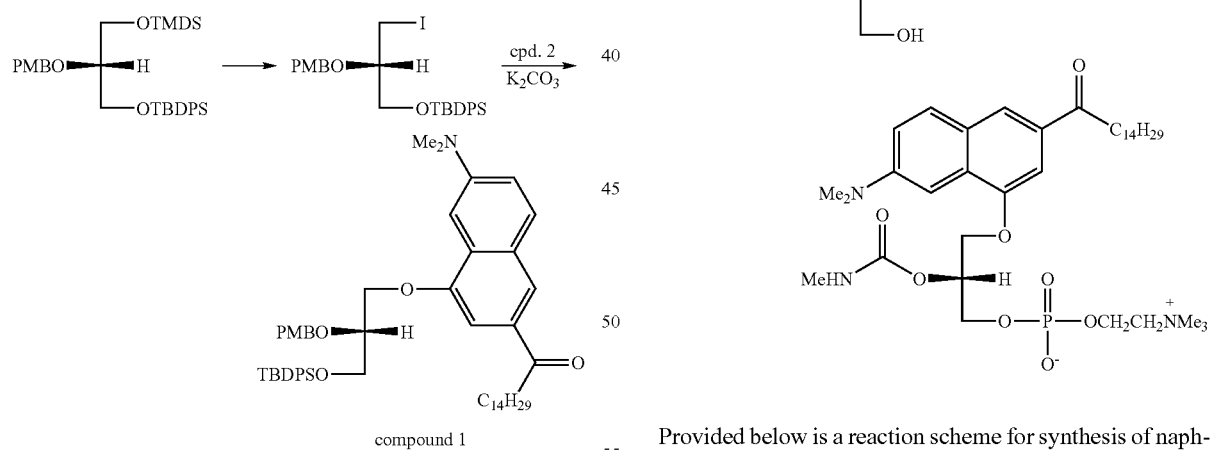

Provided below is a reaction scheme for synthesis of naphthol carbamoyl phosphonocholine derivative. The naphthol derivative of a carbamoyl phosphonocholine was synthesized as outlined in the accompanying scheme. The requisite four-carbon backbone of the phosphonolipid was prepared by using malic acid as the starting material. Arbuzov reaction of the primary bromide afforded the diethyl phosphonate ester. After installation of the carbamoyl moiety, the reaction sequence of desilylation, tosylation, and $S_N^2$ displacement with iodide ion furnished iodobutyl phosphonate compound 1. Coupling with naphthol compound 2, followed by conversion of the phosphonate to the phosphonocholine, afforded the napthol carbamoyl phosphonocholine product.

Synthesis of Naphthol Carbamoyl Phosphonocholine Derivative

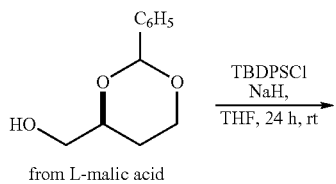

from L-malic acid

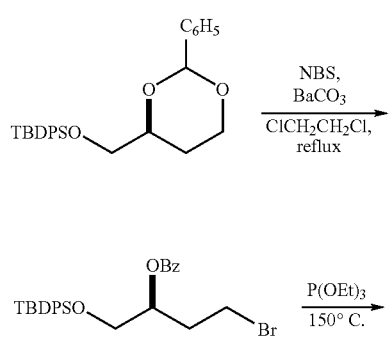

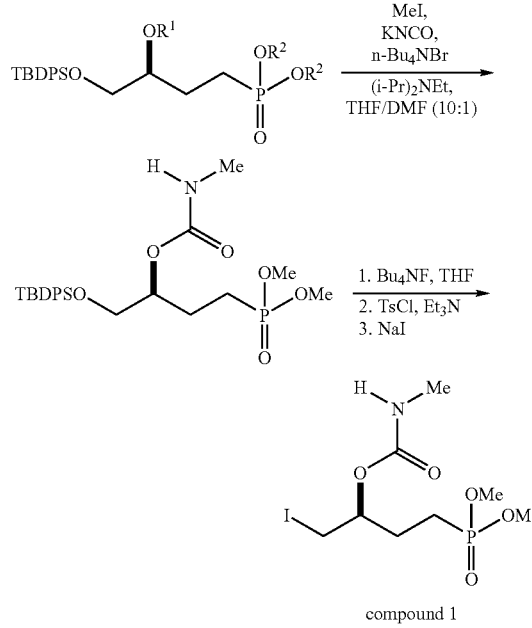

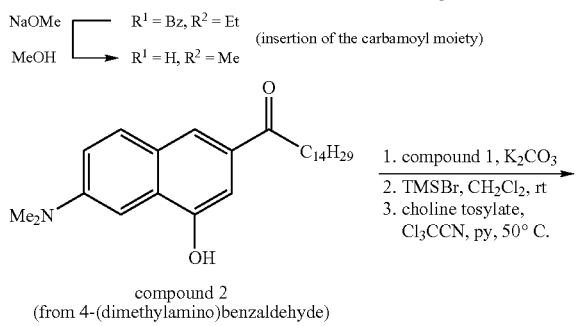

compound 2
(from 4-(dimethylamino)benzaldehyde)

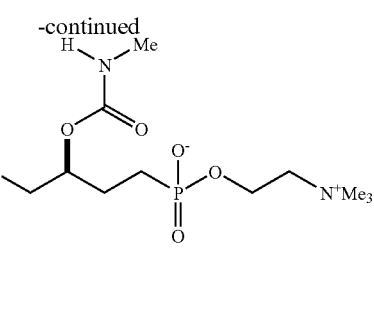

The enantiomer can be synthesized from D-malic acid

Therapeutic Methods and Uses

One method by which the compounds may have an antitumor effect is by acting as an antiproliferative agent. One aspect the present invention relates to a method of inhibiting cell proliferation by administering an effective amount of the carbamate lipids and dicarbamate lipids to humans or other animals in need. Another method by which the carbamate, dicarbamate, and ureido lipids may have an antitumor effect is by inducing death of the cancer cells. Thus another aspect of the invention provides a means of inducing cancer cell death by administering an effective amount of the carbamate and dicarbamate lipids.

The carbamate and dicarbamate lipids (compounds I-V) and uereido and their C-glycoside derivatives (compounds VI-VIII) in the invention can be used for treatment of all forms of cancer, malignant disease of hyperproliferative diseases. These include but are not limited to breast cancer, leukemias, lymphomas (Hodgkins and non-Hodgkins), plasmacytomas, histiocytomas, melanomas, adenomas, sarcomas, carcinomas of solid tissues, hypoxic tumors, squamous cell carcinomas, genitourinary cancers such as cervical, ovarian, prostate, and bladder cancers, head and neck cancers, and nervous system cancer.

Compounds I, II, and III may be particularly useful for the selective treatment of prostate cancer, both the hormone-dependent and hormone-independent forms, by administering lower doses with minimal effects on other cells. They may be used in conjunction with hormone deprivation to eradicate residual malignant prostate cells that may cause the recurrence of the hormone-independent form of the disease.

The carbamate, dicarbamate, and ureido lipids described in this invention may allow for the treatment of tumors resistant to chemotherapy including multi-drug resistant varieties and may also allow for more effective radiotherapy of tumors that currently respond poorly to radiotherapy such as adenocarcinomas of the bowel and lung. The compounds described herein may also be used in autologous bone marrow transfer, to purge the marrow stem cells of cancer cells prior to reintroducing the stem cells back into the patient.

The carbamate, dicarbamate, and ureido lipids of the present invention may also be used in combination with other antineoplastic drugs for effective treatment of tumors. This includes known conventional drugs such as antimetabolites, alkylating agents, antimicrobial antineoplastics, antimicrotubular agents, cisplatinum and its derivatives, and topoisomearase-interactive agents.

Pharmaceutical Compositions.

The ether glycerolipid carbamates of the invention may be incorporated into a pharmaceutical composition which may be useful for cancer treatment. The pharmaceutical compositions of the invention can be prepared by known methods for the preparation of pharmaceutically acceptable compositions which can be administered to patients so that effective quantities of the active compound is combined with an acceptable vehicle. The pharmaceutical compositions of the invention can be for oral, topical, rectal, parenteral, local, intravenous, inhalant, or intracerebral. They may be solid or semisolid in the form of pills, tablets, creams, ointments, gelatin capsules, capsules, slow-release capsules or pills, suppositories, soft gelatin capsules, gels, membranes, tubelets, and sprays. For parental and intracerebral use, those forms for intramuscular or subcutaneous administration can be used, or forms for infusion or intravenous or intracerebral injection can be used, and can therefore be prepared as solutions of the active compounds or as powders of the active compound mixed with one or more pharmaceutically acceptable excipients or diluents, suitable for use as described above with the osmolarity compatible with the physiological fluid.

While the preferred embodiments of the invention have been described above, it will be recognized and understood that various modifications may be made therein, and the appended claims are intended to cover all such modifications which may fall within the spirit and scope of the invention.

REFERENCES

Arthur, G. and Bittman R. (1998). The inhibition of cell signaling pathways by antitumor ether lipids. Biochim. Biophys. Acta 1390, 85-102.

Ashagbley, A., Samadder, P., Bittman, R., Erukulla, R. K., Byun, H.-S., and Arthur, G. (1996). Synthesis of ether linked analogs of lysophosphatidate and their effect on the proliferation of human epithelial cancer cells in vitro. Anticancer Res. 16, 1813-1818.

Berdel, W. E. (1991). Membrane interactive lipids as experimental anticancer drugs. Br. J. Cancer 64, 208-211.

Berdel, W. E., Andreesen, R., and Munder, P. G. (1985). In Phospholipids and Cellular Regulation. Kuo, J. F., Ed., Vol. 2, pp. 41-73, CRC Press, Boca Raton, Fla.

Bittman, R. and Arthur, G. (1999). Antitumor ether lipids: biological and biochemical effects. In Liposomes: Rational Design, Janoff, A. S., Ed., Marcel Dekker, New York, pp. 125-144 (1999).

Budman, D. R., Calabro, A., and Kreis, W. (2002). Synergistic and antagonistic combinations of drugs in human prostate cancer cell lines in vitro. Anti-Cancer Drugs 13, 1011-1016

Hanessian, S., and Plessas, N. R. (1969). J. Org. Chem. 1969, 34, 1035-1044.

He, L., Wanunu, M., Byun, H.-S., and Bittman, R. (1999). Regioselective and stereospecific azidation of 1,2- and 1,3-diols by azidotrimethylsilane via a Mitsunobu reaction. J. Org. Chem. 64, 6049-6055.

Houlihahn, W. J., Lohmeyer, M., Workman, P., and Cheon, S. H. (1995). Phospholipid antitumor agents. Med. Res. Rev. 15, 157-223.

Jacobs, S. C. (1983). Spread of prostatic cancer to bone. Urology 21, 337-344.

Jemal, A., Murray, T., Samuels, A., Ghafoor, A., Ward, E., and Thun, M. J. (2003). Cancer Statistics. CA Cancer J. Clin. 53, 5-26.

Koutsilieras, M., and Tolis, G. (1985). Long term follow-up of patients with advanced prostatic carcinoma treated with Buserelin (hoe 766) or orchiectomy: classification of variables associated with disease outcome. Prostate 7, 31-39.

Koutsilieris, M., Faure, N., Tolis, G., Larouche, B., Robert, G., and Ackman, C. F. (1986). Objective response and disease outcome in 59 patients with stage D2 prostatic cancer treated with either Buserilin or orchiectomy. Disease aggressivity and its association with response and outcome. Urology 27, 221-228.

Kreis, W., Budman, D. R., and Calabro, A. (1979). Unique synergism or antagonism of combinations of chemotherapeutic and hormonal agents in human prostate cancer cell lines. Br. J. Urol. 79, 196-202.

Lohmeyer, M., and Bittman, R. (1994) Antitumor ether lipids and alkylphosphocholines. Drugs Future 19, 1021-1037.

Lu, X., Zhou, X., Kardash, D., and Arthur, G. (1993). Metabolism of alkyllysophospholipid in epithelial cancer cell lines and inhibition of cell growth. Biochem. Cell Biol. 71, 122-126.

Mollinedo, F., Gajate, C., Martin-Santamaria, S., and Gago, F. (2004). ET-18-OCH3 (edelfosine): a selective antitumour lipid targeting apoptosis through intracellular activation of Fas/CD95 death receptor. Curr. Med. Chem.11, 3163-3184.

Navone, N. M., Logothetis, C. J., von Eschenbach, A. C., and Troncoso, P. (1999). Model systems of prostate cancer: Uses and limitations. Cancer Metastasis Rev. 17, 361-371.

Ponpipom, M. M., and Bugianesi, R. L. (1984) Chem. Phys. Lipids, 35, 29-37.

Saitoh, H., Hilda, M., Shimbo, T., Nakamura, K., Yamagata, J., and Satoh, T. (1984). Metastatic patterns of prostatic cancer. Correlation between sites and number of organs involved. Cancer 54, 3078-3084.

Samadder, P., and Arthur, G. (1999). Decreased sensitivity to 1-O-octadecyl-2-O-methyl-glycerophosphocholine in MCF-7 cells adapted for serum-free growth correlates with constitutive association of Raf-1 with cellular membranes. Cancer Res. 59, 4808-4815.

Samadder, P., Bittman, R., Byun, H.-S., and Arthur, G. (2004). Synthesis and use of novel ether phospholipids enantiomers to probe the molecular basis of the enantiomer effects of alkyllysophospholipids: correlation of differential activation of c-Jun-NH2-terminal protein kinase with antiproliferative effects in neuronal tumor cells. J. Med. Chem. 47, 2710-2713.

Sobel, R. E., and Sadar, M. D. (2005). Cell lines used in prostate cancer research: a compendium of old and new lines—Part 1. J. Urol. 173, 342-359.

van Boeckel, C. A. A., van del Marel, G. A., Westerduin, P., and van Boom, J. H. (1982) Synthesis 1982, 399-402.

Yang, G., Franck, R. W., Byun, H.-S., Bittman, R., Samadder, P., and Arthur, G. (1999). Convergent C-glycolipid synthesis via the Ramberg-Backlund reaction: active antiproliferative glycolipids. Org. Lett. 1, 2149-2151.

TABLE 1

Growth Inhibitory Properties of Carbamate and Dicarbamate Lipid Compounds I-V on Human Tumor Cells [reported as IC$_{50}$ (μM)]

| Cell Line | I | II | III | IV | V |
|---|---|---|---|---|---|
| DU145, prostate | 1.2 | 2.1 | 2.4 | 4.8 | 8.2 |
| PC3, prostate | 1.2 | 2.5 | 1.9 | 2.8 | 4.1 |
| BT549, breast | 4.4 | 6.8 | 13.4 | 4.9 | 6.6 |
| MDA-MB-231, breast | 3.7 | 6.1 | 10.5 | 18.3 | 6.6 |
| MCF-7, breast | 4 | 10.1 | 9.1 | 13.4 | >20 |
| HeLa, cervix | 3.3 | 7.9 | 19.3 | 8.7 | 14.9 |
| A549, lung | 10.7 | >20 | >20 | >20 | >20 |

IC$_{50}$ is the drug concentration (μM) required to inhibit the growth by 50% after incubation of exponentially growing cells with the drug for 48 hours.

TABLE 2

Antiproliferative effect of 1-O(7-N,N-dimethylamino-3-pentadeconyl-1-naphthyl)-2-O-methyl-sn-glycero-3-phosphocholine against human cancer cells

| Cancer Cell Line | IC$_{50}$ μM |
| --- | --- |
| SK-N-SH (neuronal) | <20 |
| SK-N-MC (neuronal) | >20 |
| DU145 (prostate) | 3.5 |
| PC3 (prostate) | 1.9 |
| MCF-7 (breast) | >20 |
| HepG2 (liver) | >20 |
| A549 (lung) | >20 |

Proliferating cells in 48-well plates were incubated with 0-20 μM of the compound for 48 h. The cell numbers present were determined by the CyQuant™ assay (Invitrogen), and the increase in numbers were expressed relative to the controls receiving only the vehicle (0.1% ethanol).

The invention claimed is:

1. A method of treating prostate cancer in a patient comprising administering to a patient in need of such treatment an effective amount of a compound having a formula selected from the group consisting of:

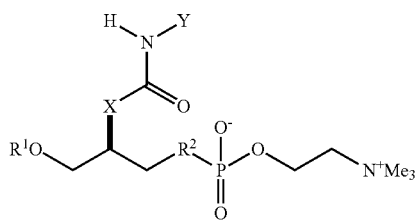
(I)

X = O or NH
Y = Me or OH
R$^1$ = C$_{12}$-C$_{20}$ alkyl or C$_{12}$-C$_{20}$ alkenyl
R$^2$ = CH$_2$

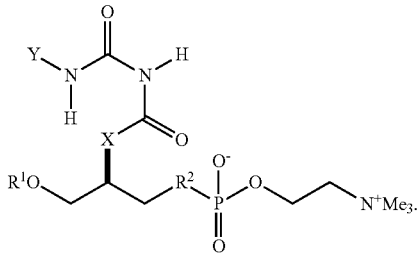
(II)

X = O or NH
Y = Me or OH
R$^1$ = C$_{12}$-C$_{20}$ alkyl or C$_{12}$-C$_{20}$ alkenyl
R$^2$ = O or CH$_2$ 2. The method according to claim 1 wherein the compound is a compound of Formula (I) and Y is Me.

3. The method according to claim 1 wherein the compound is a compound of Formula (I) and X is O.

4. The method according to claim 1 wherein the compound is a compound of Formula (I) and R$^1$ is C$_{12}$-C$_{20}$ alkyl.

5. The method according to claim 1 wherein the compound is a compound of Formula (I) and Y is methyl and X is O.

6. The method according to claim 5 wherein the compound is a compound of Formula (I) and R$^1$ is C$_{12}$-C$_{20}$ alkyl.

* * * * *